(12) United States Patent
Sausa et al.

(10) Patent No.: US 9,335,267 B2
(45) Date of Patent: May 10, 2016

(54) NEAR-IR LASER-INDUCED VIBRATIONAL OVERTONE ABSORPTION SYSTEMS AND METHODS FOR MATERIAL DETECTION

(71) Applicant: U.S. Army Research Laboratory, Washington, DC (US)

(72) Inventors: Rosario Sausa, Newark, DE (US); Jerry B. Cabalo, Towson, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 661 days.

(21) Appl. No.: 13/748,874

(22) Filed: Jan. 24, 2013

(65) Prior Publication Data

US 2014/0060189 A1  Mar. 6, 2014

Related U.S. Application Data

(60) Provisional application No. 61/669,205, filed on Jul. 9, 2012.

(51) Int. Cl.
| | | |
|---|---|---|
| G01H 1/00 | (2006.01) | |
| G01N 21/64 | (2006.01) | |
| G01N 21/3563 | (2014.01) | |
| G01N 21/359 | (2014.01) | |

(52) U.S. Cl.
CPC .......... G01N 21/6402 (2013.01); G01N 21/359 (2013.01); G01N 21/3563 (2013.01)

(58) Field of Classification Search
CPC .......... G01N 21/6402; G01N 21/3563; G01N 21/359
See application file for complete search history.

(56) References Cited

U.S. PATENT DOCUMENTS

| | | | | |
|---|---|---|---|---|
| 4,496,839 | A | 1/1985 | Bernstein et al. | |
| 5,363,398 | A * | 11/1994 | Glass | C09K 11/7706 372/45.01 |
| 5,377,219 | A * | 12/1994 | Geiger | G01S 7/4811 356/301 |
| 5,478,658 | A * | 12/1995 | Dodabalapur | H01L 51/5265 313/504 |
| 6,646,264 | B1 * | 11/2003 | Modiano | G01N 21/359 250/339.07 |
| 7,123,359 | B2 * | 10/2006 | Armstrong | B82Y 10/00 356/301 |

(Continued)

OTHER PUBLICATIONS

A. Bell, "Upon the production of sound by radiant energy". Paper read at National Academy of Sciences, Apr. 21, 1881, Washington D.C.: Gibson Brothers Printers, 1881.

(Continued)

Primary Examiner — Laura Martin
Assistant Examiner — Samir M Shah
(74) Attorney, Agent, or Firm — Eric B. Compton

(57) ABSTRACT

Embodiments of present invention are directed to near infrared (IR) laser-induced vibrational absorption systems and methods for material detection. According to one embodiment, a system for detecting materials may include: at least one laser configured to output light in the near IR spectrum so as to excite at least one vibrational overtone frequency, at least one combination band frequency, or a combination thereof, of a sample comprised of one or more of materials; a detector configured to detect a physical phenomenon of the sample in response to laser excitation; and an analyzer configured to the analyze the detected physical phenomenon and to identify the one or more materials based comparison of the detected signatures with known signatures of one more materials.

20 Claims, 22 Drawing Sheets

(56) References Cited

U.S. PATENT DOCUMENTS

| | | | | |
|---|---|---|---|---|
| 7,336,351 | B1* | 2/2008 | Sweatt | G01J 3/02 356/244 |
| 7,532,320 | B2* | 5/2009 | Neiss | G01J 3/02 356/301 |
| 7,861,574 | B2 | 1/2011 | Sheen et al. | |
| 7,990,532 | B2* | 8/2011 | Neiss | G01J 3/28 356/301 |
| 8,154,399 | B2* | 4/2012 | Pellegrino | G08B 21/12 340/506 |
| 8,400,348 | B1* | 3/2013 | Guice | A01M 1/026 235/400 |
| 8,409,863 | B2* | 4/2013 | Natan | G01N 21/658 436/171 |
| 9,012,241 | B2* | 4/2015 | Han | G01N 33/54346 435/7.1 |
| 9,201,013 | B2* | 12/2015 | Natan | B22F 1/0018 |
| 2002/0015150 | A1* | 2/2002 | Armstrong | G02F 1/355 356/301 |
| 2002/0025490 | A1* | 2/2002 | Shchegolikhin | B41M 3/14 430/270.15 |
| 2004/0150818 | A1* | 8/2004 | Armstrong | B82Y 10/00 356/301 |
| 2006/0063188 | A1* | 3/2006 | Zanni | G01N 21/35 435/6.18 |

OTHER PUBLICATIONS

A. Rosencwaig and A. Gersho, "Theory of the photoacoustic effect with solids." J. Appl. Phys., 47(1), 64 (1976).

D. Moore, "Instrumentation for trace detection of high explosives" Rev. Sci. Instrum. 2004. 75(8): 2499-2512.

A. Rubenchik, "On the Initiation of High Explosives by Laser Radiation," Propellants, Explosives, Pyrotechnics, 32(4), 296 (2007).

E Holthoff et al. "Quantum Cascade Laser-Based Photoacoustic Spectroscopy for Trace Vapor Detection and Molecular Discrimination," Sensors 2010, 10, 1986-2002.

J. Cabalo, "Investigation of Molecule-Surface Interactions with Overtone Absorption Spectroscopy and Computational Methods," ECBC-TR-821, Nov. 2010.

J. Cabalo and R. Sausa, "Investigation of Molecule-Surface Interactions with Overtone Absorption Spectroscopy and Computational Methods," Proceedings of the 27th Army Science Conference, Dec. 2010.

Department of Navy Letter dated May 14, 2012 regarding licensing of, and including a copy of U.S. Appl. No. 13/292,379, filed Nov. 9, 2011.

J.B. Cabalo and R.Sausa, "Experimental and Theorectical Investigation of the First Overtone Spectrum of 1,3,5-Trinitrotoluene," The Journal of Physical Chemistry, vol. 115, pp. 9139-9150 (2011).

R. Sausa and J. Cabalo, "Photoacoustic spectroscopy and modeling of energetic materials" (Abstract only submitted and distributed to attendees; presentation made at meeting), Proceedings of the 242nd American Chemical Society Meeting, Boulder, CO, Aug. 29, 2011.

E. Holthoff et al., "Quantum Cascade Laser Based Photoacoustic Spectroscopy for Depth Profiling Investigations of Condensed-Phase Materials," Applied Spectroscopy, vol. 66, Issue 9, pp. 987-992 (2012).

R. Sausa and J. Cabalo, "The Detection of Energetic Materials by Laser Photoacoustic Overtone Spectroscopy," Applied Spectroscopy, vol. 66, Issue 9, pp. 993-998 (2012).

"MTEC Photoacoustics, Inc—PAC 300 Photoacoustic Detector" Website, available at: http://www.speciation.net/Database/Instruments/MTEC-Photoacoustics-Inc/PAC-300-Photoacoustic-Detector-;i1532 (accessed Mar. 7, 2012).

* cited by examiner

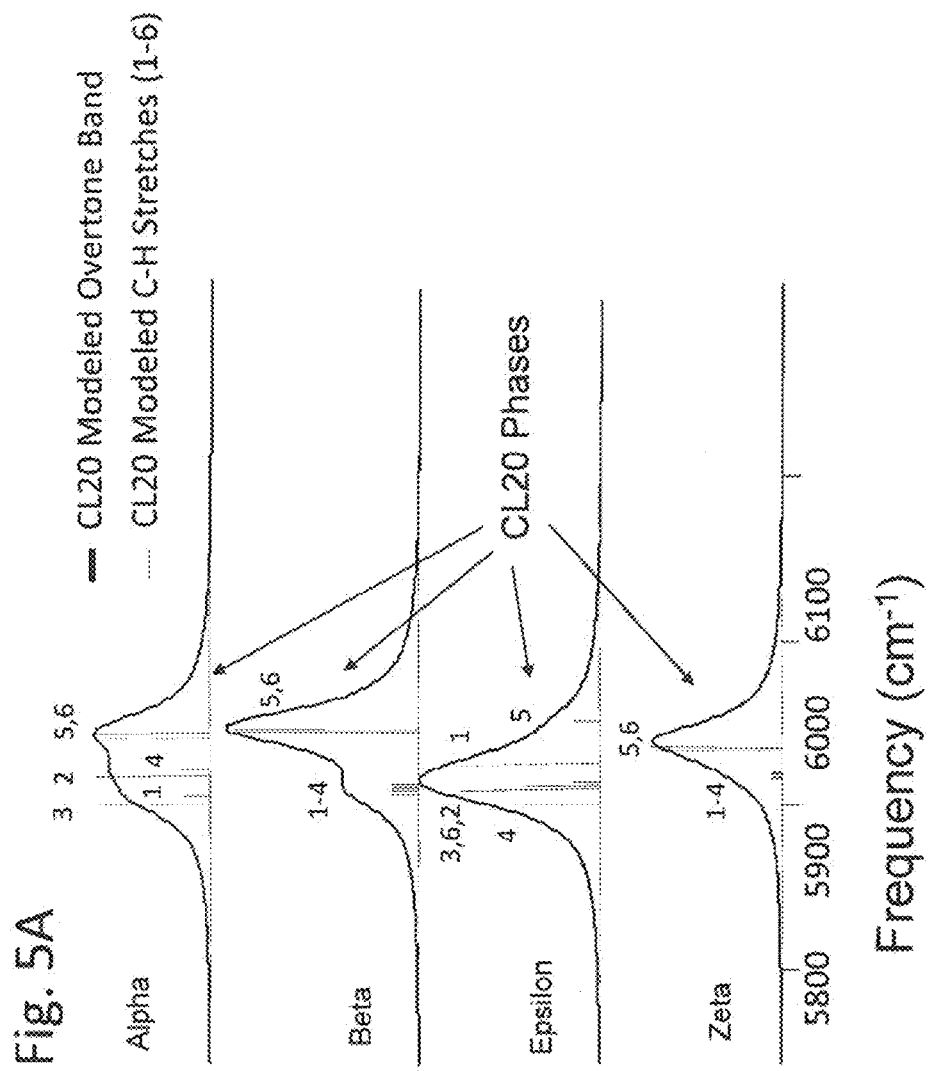

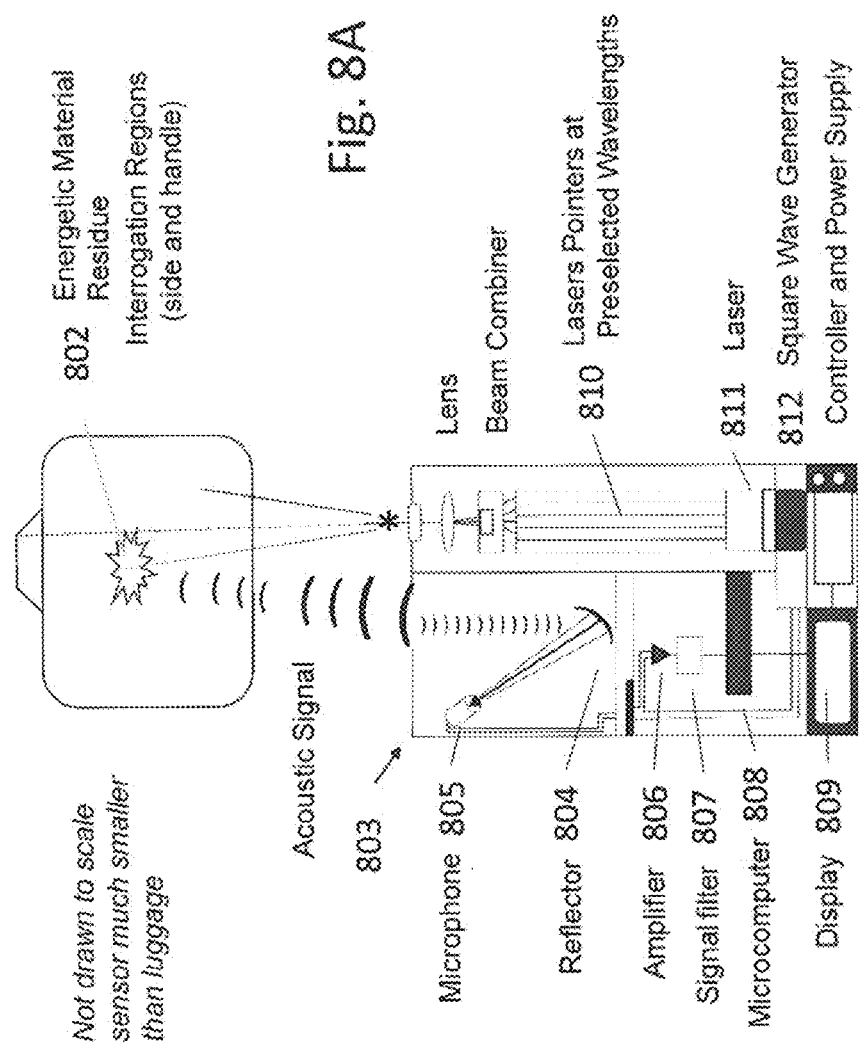

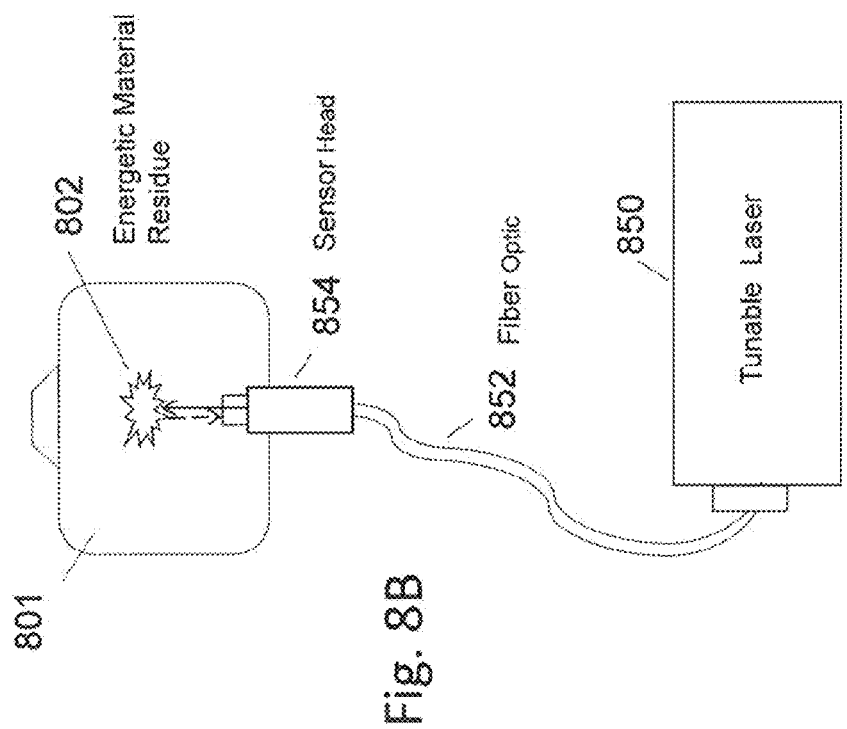

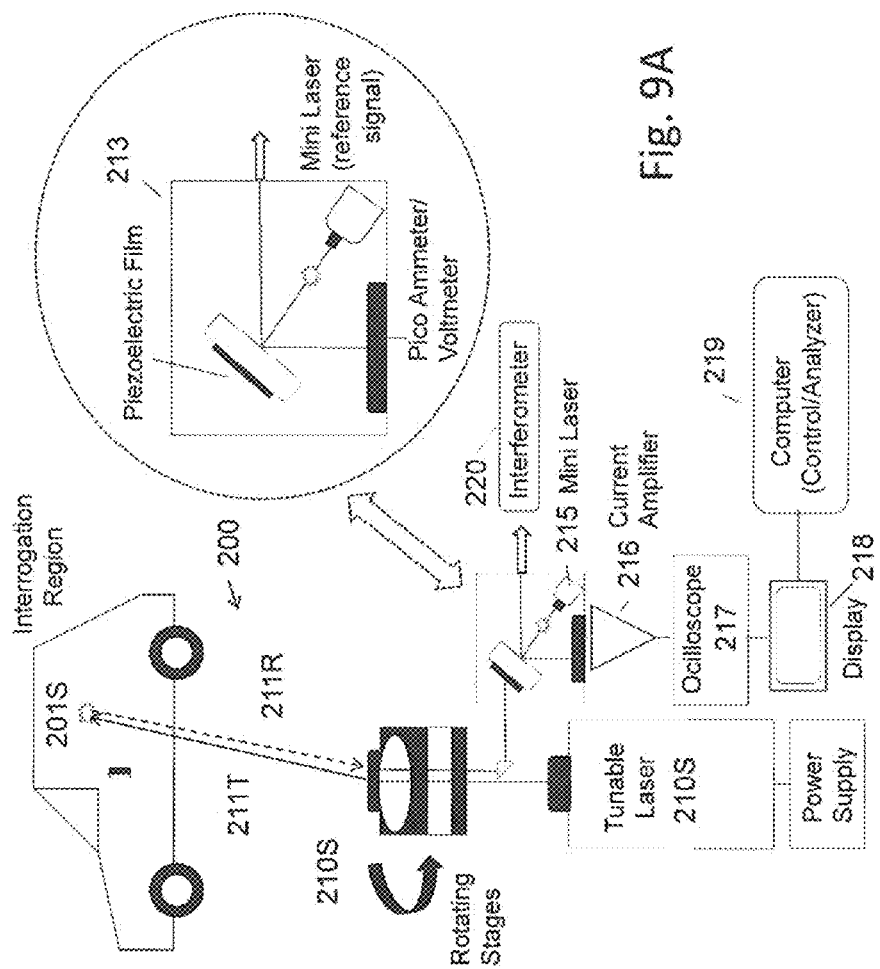

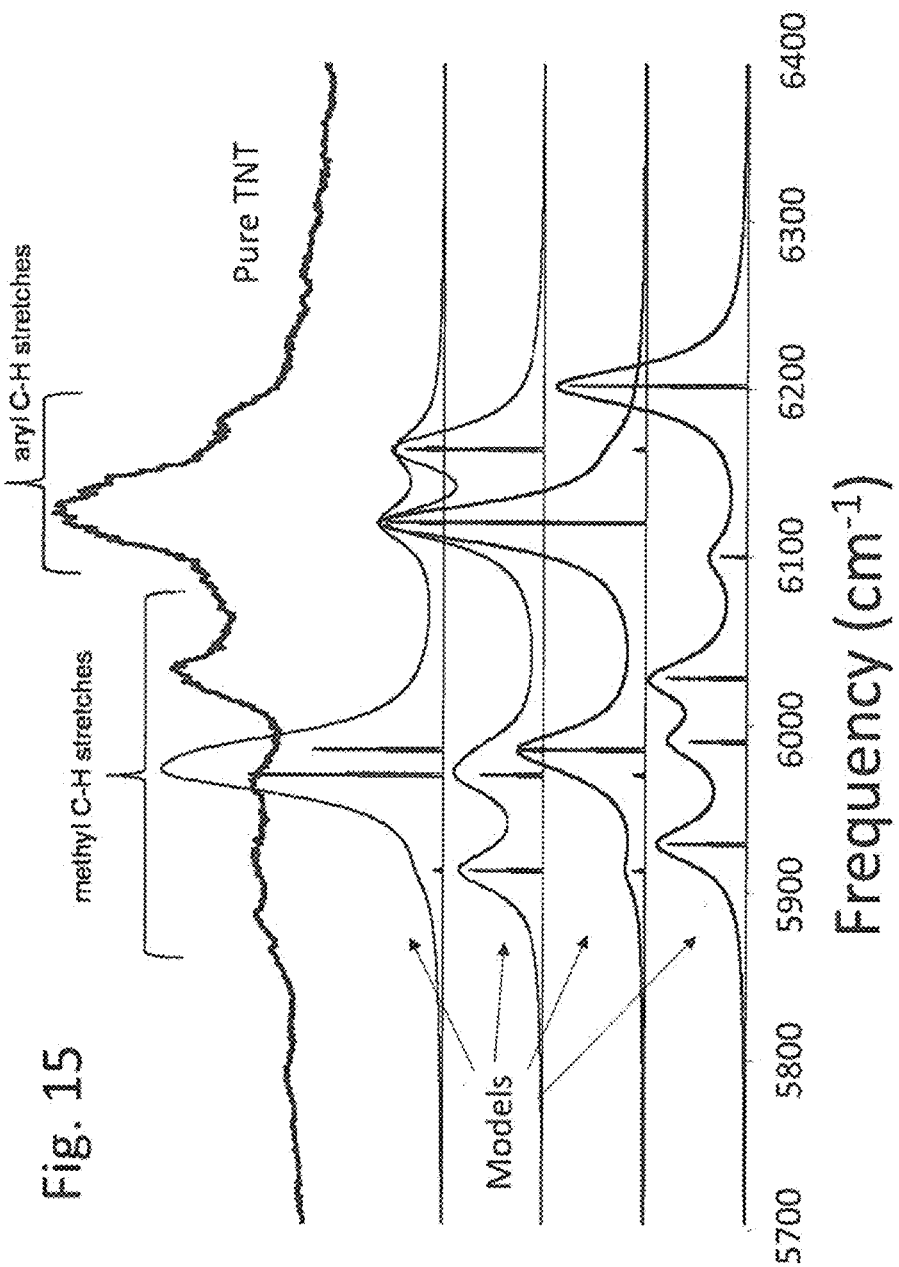

NEAR-IR LASER-INDUCED VIBRATIONAL OVERTONE ABSORPTION SYSTEMS AND METHODS FOR MATERIAL DETECTION

CROSS REFERENCE TO RELATED APPLICATION(S)

The present application claims the benefit of U.S. Provisional Application No. 61/669,205 entitled "Near-IR Laser-induced Vibrational Overtone Absorption Systems and Methods for Material Detection" filed Jul. 9, 2012, herein incorporated by reference as though described in its entirety herein.

GOVERNMENT INTEREST

The invention described herein may be manufactured, used and licensed by or for the U.S. Government without the payment of royalties thereon.

BACKGROUND OF THE INVENTION

1. Field

Embodiments of the present invention generally relate to the detection of materials, including hazardous and explosive materials.

2. Related Art

Detection of materials, such as energetic or explosive materials, toxic industrial chemicals, and chemical agents, is of great importance for various military and homeland security applications. Energetic materials may include 1,3,5-trinitrotoluene (TNT), 1,3,5-trinitro-1,3,5-triazacyclohexane (RDX), 2,4,6,8,10,12-hexanitro-2,4,6,8,10,12-hexaazoisowurtzitane (CL20), for instance.

Conventional methods for detection of energetic materials, however, pose a challenge because these materials typically have very low vapor pressures and present a minimal amount of material to conventional detectors that sense vapors. As such, these materials may be difficult to detect spectroscopically at ambient conditions. The difficulty stems in part because they do not emit sufficient vapors at atmospheric pressure for their sensing. For example, RDX has a vapor pressure of about $5 \times 10^{-9}$ torr (app. $7 \times 10^{-7}$ Pascal) or 7 ppt/v (parts per trillion by volume) at ambient conditions, which is about three orders of magnitude less than TNT. Other hazardous compounds, such as some chemical nerve agents, e.g. VX, also have low vapor pressures at ambient conditions, and thus present a similar challenge for their detection. An added complication is that vapor molecules of energetic materials and other materials tend to readily adsorb to surfaces, so that molecules available for detection are reduced further. Material detection by light emission and/or absorption is challenging because the resulting spectra lack distinguishable features, particularly in the ultraviolet and visible region of the electromagnetic spectrum, the emissions signals are quenched by collisions at atmospheric pressure, or a combination thereof.

Numerous methods and devices have been developed to reduce the risk to the general population and military personnel by detecting the presence of materials. For instance, ion mobility spectrometry (IMS) with detection limits on the order of 1-10 ppb is the current state of the art for sensing vapors and is commonly in use in airports and other secured areas. This detection limit is still higher than the vapor pressures of many relevant energetic materials.

Laser-based strategies also exist for detecting energetic materials on surfaces. Some laser spectroscopic strategies include laser induced breakdown spectroscopy (LIBS), laser photofragmentation—fragment detection (PF-FD), and Raman spectroscopy. LIBS uses high-powered, focused laser beams to completely break down a complex energetic material into its constituent elements. When using LIBS as a detection technique, the breakdown of energetic material into atomic constituents can hinder positive energetic material identification. In contrast, PF-FD breaks down the complex explosive molecule into larger fragments or signature molecular groups such as $NO_2$ and NO that are subsequently detected by UV laser induced fluorescence (LIF) and/or resonance-enhanced multiphoton ionization (REMPI), thus indicating the presence of the energetic material. Both LIBS and PF-FD are indirect methods for energetic materials detection. They do not identify the energetic materials, but instead identify characteristic fragments resulting from the photolysis or decomposition of the energetic materials. As a result, the selectivity of these methods is not as high as those that involve direct detection. Also, trace quantities of atmospheric nitrous oxide ($NO_2$) may interfere with the measurements. This potentially leads to high false positive rates.

Raman spectroscopy is a laser-based approach that has proven successful to detect directly energetic materials. The technique uses a laser to probe the molecule's fundamental vibrational and rotational states from the inelastic scatter of photons. However, without UV resonance enhancement, Raman spectroscopy suffers from weak signals. Furthermore, practical Raman instruments require high resolution dispersive elements and an arrayed charge-coupled device (CCD), or complementary metal-oxide-semiconductor (CMOS) detector arrays, resulting in complex electronics. Additional electronics lead to high complexity and power consumption.

Photoacoustic spectroscopy may be used for detecting energetic materials. Alexander Graham Bell discovered the photoacoustic effect in 1881, when he found that materials emit sound when exposed to a rapidly interrupted beam of sunlight. The sample converts part of the absorbed laser light into heat, which can be transferred to the ambient air. The pressure fluctuation caused by rapid sample heating and cooling appears as compression and rarefaction of the air and results in sound. Absorption features in the ultraviolet, visible, or infrared region of the electromagnetic spectrum correspond to a molecule's electronic (ultraviolet and visible) or vibrational transitions (infrared). Most molecules contain broad spectral features in the ultraviolet region, but exhibit sharp, well-defined features in the infrared. These defined features enhance a sensor's selectivity and, as a result, many of them employ infrared wavelengths.

Ethylene glycol dinitrate (EGDN), nitroglycerine (NG) and 2,4-Dinitrotoluene (DNT) vapors have reportedly been detected in the parts per billion using a 9.6 μm $CO_2$ laser, and spectra and models of TNT and RDX at $CO_2$ laser wavelengths ranging from 9.6 to 11.6 μm have been reported. Recently, a photoacoustic spectroscopy system and technique for remote sensing of explosives toxic chemicals was disclosed using a pulsed tunable laser such as a $CO_2$ laser to detect NG, DNT, TNT, and ammonium nitrate ($NH_4NO_3$). However, the low vapor pressure of most explosives, such as RDX and CL20, precludes their detection with this technique at ambient temperature and pressure. In the case of TNT, the sensor's signal-to-noise ratio is poor because the vapor pressure of TNT is low at ambient conditions. Also, ambient levels of $CO_2$, $NH_3$, $O_3$, and $H_2O$ interfere strongly in this spectral region.

And, more recently, remote identification of gas-phase explosives and other harmful materials by semiconducting nanoparticle photoluminescence or photoacoustics have been reported. As mentioned above, though, gas-phase detection of most explosives cannot be achieved at room temperature and pressure, and for limited cases such as TNT, the signal-to-noise is very poor. Nanoparticle luminescence is restricted to energetic materials synthesized with such particles. Most energetic materials do not contain these particles because they may lower the overall system performance or because they may help in tracking the energetic materials' origin.

Energetic materials possess vibrational absorption features which can be exploited for detecting many compounds in the vapor phase. The use of tunable cascade lasers and photoacoustics to detect trace gases, TNT, triacetone triperoxide (TATP), and precursors of acetone and hydrogen peroxide have been disclosed. While this technique may work for samples with high vapor pressures at ambient conditions, it has been shown to work very poorly for various energetic materials such as TNT because it has very little vapor pressure at ambient conditions. Solid-phase RDX and CL20 have vapor pressures that are several orders of magnitude lower than TNT at ambient conditions and they will present a formidable challenge for this technique.

Improved detection of materials would be useful.

BRIEF SUMMARY OF THE INVENTION

Embodiments of present invention are directed laser-induced vibrational overtone absorption systems and methods for material detection.

According to one embodiment, a system for detecting materials may include: at least one laser configured to output light in the near IR spectrum so as to excite at least one vibrational overtone frequency, at least one combination band frequency, or a combination thereof, of a sample comprised of one or more of materials; a detector configured to detect a physical phenomenon of the sample in response to laser excitation; and an analyzer configured to the analyze the detected physical phenomenon and to identify the one or more materials based comparison of the detected signatures with known signatures of one more materials.

According to another embodiment, a method for detecting and monitoring materials may include: exciting at least one vibrational overtone frequency, at least one combination band frequency, or a combination thereof, of a sample comprised of one or more of materials using at least one laser which outputs light in the near IR spectrum; detecting a physical phenomenon of the sample in response to laser excitation; and analyzing the detected physical phenomenon to identify the one or more materials based comparison of the detected signatures with known signatures of one more materials.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. These embodiments are intended to be included within the following description and protected by the accompanying claims.

FIG. 5A schematically illustrates quantum mechanical calculations spectra of various CL20 polymorphs;

FIG. 8A is a schematic illustration of a material detection system configured as a stand-alone hand-held or robot-mounted sensor assembly according to an embodiment;

FIG. 8B is a schematic illustration of a material detection system having a hand-held sensor interfaced with tunable laser by fiber-optic according to an embodiment;

FIG. 9A is a schematic illustration of a material detection system capable of vehicular usage by probing the displacement of the material's surface using piezoelectric film according to an embodiment;

FIG. 15 is an illustration showing the laser photoacoustic overtone spectrum compared with predicted spectra from HCAO and the MP2/6-31+G(d,p) level of theory for charge assigned by the QEq/Mulliken, QEq/MSK, and HF/3-21+G* calculation/MSK. The model is optimized with the universal force field.

DETAILED DESCRIPTION OF THE INVENTION

Figure 1:
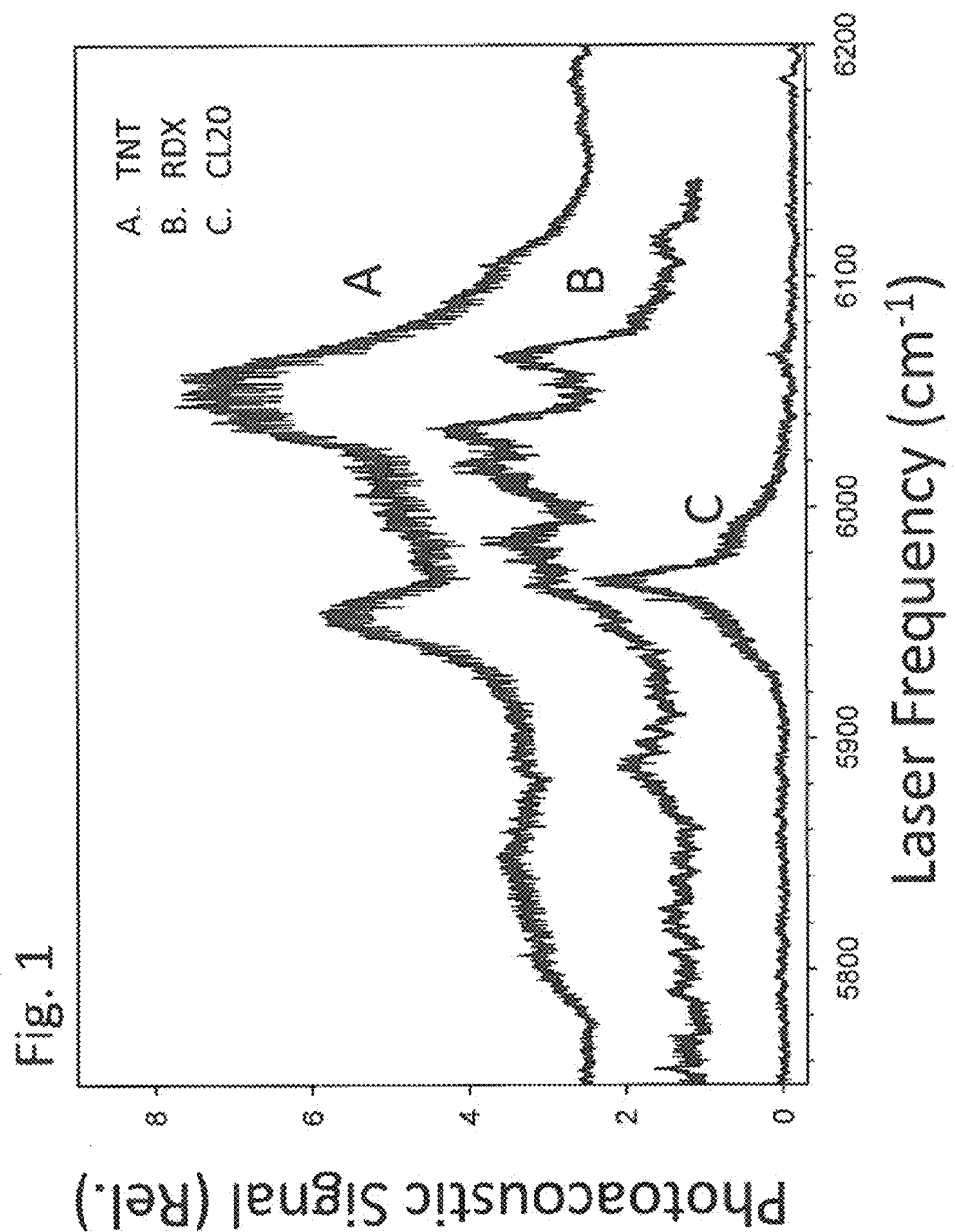
FIG. 1 illustrates photoacoustic spectra of RDX, TNT, and CL20 in the near IR region.

Embodiments of present invention are directed to laser-induced vibrational overtone absorption systems and methods for material detection by exciting at least one vibrational overtone frequency, at least one combination band frequency, or a combination thereof. One or more lasers may output light in the near infrared (IR) spectrum having wavelengths between about 0.75 to 2.0 μm in some embodiments.

An overtone or harmonic absorption is the absorption of electromagnetic energy (e.g., light) that takes a molecule from the ground vibrational state (v=0) to the second or higher vibrationally excited state (v=2, 3, 4 etc.) of a given vibrational mode. For a non-linear molecule of N atoms, there are 3N-6 vibrational modes, where each vibrational mode can absorb its own distinct optical frequency. A linear molecule has 3N-5 vibrational modes. If the fundamental frequency of a vibrational mode is defined as F, then a molecule will have 3N-6 or 3N-5 fundamental frequencies, $F_i$, where i=1, 2, 3 . . . up to 3N-5, depending on its geometry. Thus, molecular vibrational spectra are rich in molecular structure information, and each molecule has its own unique vibrational spectral fingerprint. The fundamental absorption only involves an absorption by the ground vibrational state to the first excited state (v=1) of a given vibrational mode. This type of absorption is common in standard Raman scattering or conventional mid-IR absorption spectra, as they typically involve only the fundamental vibrational frequencies.

In contrast, overtone bands are typically analogous and are multiples of the fundamental absorption frequency and provide additional signatures for identifying molecules. These bands appear typically in the near IR spectral region. For instance, the first overtone absorption may be defined as the absorption of light that takes a molecule or atom from the ground vibrational state (v=0) to the second excited vibrational state (v=2). The energy required for the first overtone is slightly less than twice the fundamental because molecules do not have equally spaced energy levels. Since energy is proportional to the frequency absorbed and this is proportional to the wavenumber, the first overtone will appear in the spectrum at approximately twice the wavenumber of the fundamental.

Combination bands arise when at least two fundamental vibrations absorb energy simultaneously. If the fundamental frequencies of two vibrational modes are $F_1$ and $F_2$, then combination bands may be found at frequencies near $nF_1 \pm mF_2$, where n and m are integer values 1, 2, 3 . . . etc.

To date, excitation of a vibrational overtone frequency and/or combination band frequency (wavelength in the 1.5 to 2.0 micron spectral region) for material detection has been overlooked and not used because the absorption cross-sections of these transitions are typically an order of magnitude less than those occurring in the fundamental absorption spectral region (3 to 4 microns).

Although the absorption cross-sections of a molecule's overtones and/or combination bands are typically less than its fundamental absorption, there are several advantages of using the overtone absorption bands of energetic materials. First, the availability of laser sources with very high output in this spectral region, up to several orders of magnitude compared to those in the fundamental absorption region, more than compensates for the relatively weaker overtone absorptions compared to the fundamental absorptions. Second, this region does not suffer from the interference from water vapor as much as other IR regions. This attribute is particularly important for remote sensing of materials by the methods and systems disclosed herein. Third, some molecules may exhibit spectral features due to combination bands near the overtone bands, thus increasing the spectral selectivity of the laser-based detection technique. Fourth, this spectral region is "eye-safe" because it offers the highest protection to the laser operator or bystander compared to other laser spectral regions. Laser wavelengths shorter than this region cause damage to the eye's retina, whereas longer wavelengths cause more damage to the cornea. Other advantages of employing overtone absorptions and/or combination bands, instead of fundamental absorptions, will be discussed below.

The disclosed systems and methods herein may be used for detection of various materials on many different surfaces near or at ambient conditions, i.e., −20° C. to 55° C., 0-100% Relative Humidity, and near or at standard ambient pressure (e.g., 760 mm/Hg or $10^5$ Pascal at 25° C.). Detected materials may include various materials, such as, for example, energetics, explosives, propellants, chemical warfare agents, industrial pollutants, and other hazardous materials or benign materials in various environments, for instance.

Moreover, they may be used for detecting very small or trace amounts of materials, on the order of 1 nanogram (ng), even for materials that have low or no vapor pressure.

In various embodiments, non-contact, detection systems for materials are disclosed. The systems utilize near IR electromagnetic energy (light) to stimulate or otherwise excite overtone absorptions or combination thereof in a suspect material. The light may be generated by a laser, for example.

In response to this stimulation, compounds and molecules of the suspect material may become excited and expresses a physical phenomenon. In some embodiments, the suspect material emits sound waves due to the photo-acoustic effect. This sound results from the conversion of laser absorbed energy into heat, i.e., non-radiative process. Photoacoustic absorption spectra for these compounds reveal that each spectrum is unique to each measured material and can serve as a fingerprint for that material. Unlike most optically-based detection methods, photoacoustic methods are highly insensitive to light scattering by substrates and are only sensitive to actual absorption of optical radiation. Thus, absorption measurements of rough surfaces, such as pavement, sand, stone, etc, can be examined without the need for accounting for extinction due to light scattering. Alternatively or additionally, molecules of a suspect material can also ionize and/or emit radiation, once excited by laser radiation.

A detector may be configured to detect or measure the physical phenomenon. In the case of measuring sound waves, a microphone may be provided, for instance. Other detectors may be used for measuring or detecting other physical phenomenon generated when overtone vibrational bands absorb optical energy. From detected data, a signature of the suspect explosive can be generated and analyzed by an analyzer. The analyzer may search or compare detected sensor data against a library or database of known material signatures to determine one or more "best" matches, for example.

Indeed, laboratory experiments conducted by the inventors show that explosives and families of explosives have unique signatures which may be detected and identified using near IR, laser-induced vibrational overtone absorption. Other types or families of molecules may be likewise detected and identified in this manner.

As mentioned above, near IR light may be utilized to excite suspect materials. This includes electromagnetic energy (light) having wavelengths between about 0.75 to 2.0 µm. Although other optical wavelengths are suitable for photoacoustic spectroscopy, such as mid-IR wavelengths, the inventors have found that near-IR wavelengths are advantageous in that they overcome a number of technical limitations associated with other wavelengths such as visible, ultraviolet (UV), and infrared wavelengths including those from mid-IR (e.g., 3-12 µm) to far-IR (e.g., greater than 250 µm). Some of these technical limitations are as follows:

First, lasers operating in the near-IR are capable of high, tunable outputs up to hundreds of milli-Watts without requiring cryogenic or thermo-electric cooling. On the other hand, the cooling requirements of mid-IR quantum cascade lasers impose severe limitations on sensors based on those light sources in terms of power consumption, size, weight, and cost. Second, unlike quantum cascade lasers, which operate mostly in a narrow spectral range (app. 100 cm$^{-1}$) in the wavelength region 6-12 µm, and $CO_2$ lasers, whose output is restricted to tens of descrete wavelengths in the wavelength region 9-11 µm, near-IR lasers can be tuned over the entire near-IR spectral region (e.g., 0.75-2 µm). Third, near-IR wavelengths do not suffer from interference from water vapor as much as the mid-IR and far-IR wavelengths. This attribute is particularly important for remote sensing applications. Fourth, unlike ultraviolet and visible wavelengths, as would be used, for example, with Raman detection, near-IR wavelengths generally pose no significant issue for human sight. This spectral region is "eye-safe" because it offers the highest protection to the laser operator, suspect, or bystander compared to other laser spectral regions. Laser wavelengths shorter than this region cause damage to the eye's retina, whereas longer wavelengths cause more damage to the eye's cornea.

Some of the disclosed detection systems lend themselves to rapid "in-field" or in-situ detection of suspect materials without having to prepare the suspect materials for detection compared with a laboratory setting. Moreover, by providing remote detection systems, users may be kept at a safe distance (e.g., up to tens of meters or more) from the suspect explosive or other dangerous or hazardous materials. Of course, detection systems according to embodiments of the present invention may also be used in the laboratory setting as well.

FIG. 1 shows example of spectral signature (or fingerprints) of energetic materials RDX, TNT, and CL20 in the region of 5700 to 6200 cm$^{-1}$ (corresponding to wavelengths of approximately 1.61-1.75 µm). Here, these signatures arise mostly from the first overtone absorption of the C—H stretching modes in the energetic materials.

As can be appreciated from FIG. 1, each of the energetic materials has a distinctive signature. For example, although both RDX and TNT are generally cyclic and contain various C—H molecular bond stretches. The overtone and combination bands of RDX are very distinct from the overtone bands of TNT. Thus, the sample's overtone and/or combination spectra may serve as a basis of their identification. In experiments, the inventors employed an optical parametric oscillator laser because it is continuously tunable in the optical wavelength range of interest. However, signature information can be obtained also with a few discrete wavelengths.

Figure 2A:
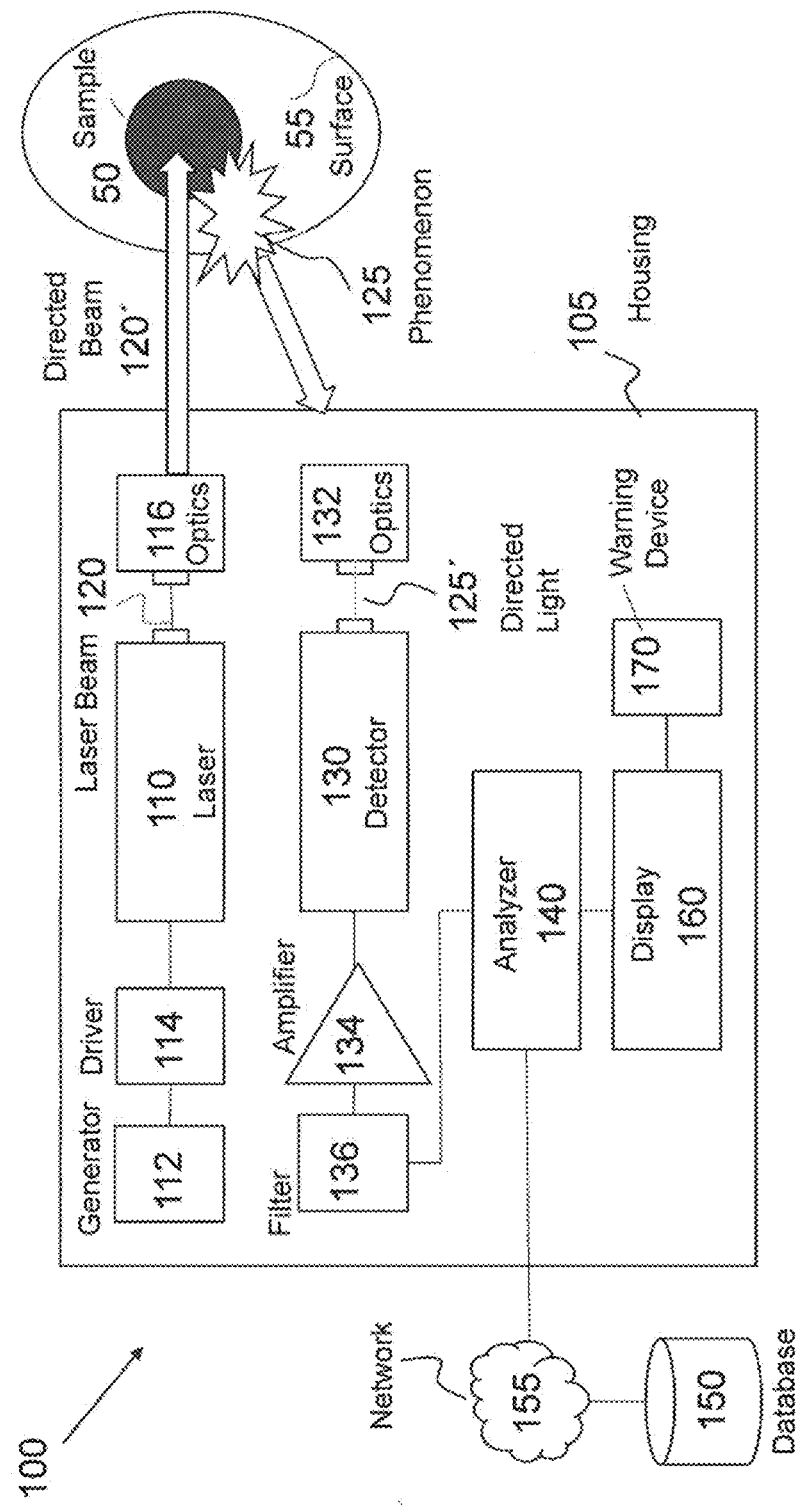
FIGS. 2A and 2B a schematic diagram of a system for detecting materials according to an embodiment.

FIG. 2A illustrates a schematic of a system 100 for detecting materials according to an embodiment of the present invention.

Various elements of the system 100 may be incorporated into a housing or other structure 105, thus forming a unitary apparatus, in some embodiments. The housing 105 may also include an appropriate power supply, for instance. As such, the system 100, embodied as an apparatus, may provide a compact and portable device with minimal power requirements, which may be mounted on an unmanned ground vehicle (UGV), robot, or other platform. Also, it might also be mounted on a hand-manipulated boom for mine or improvised explosive device (IED) detection, for example. Although, other applications are possible. In some embodiments, not all elements illustrated in the figure will be provided, and/or other elements may be provided. Additionally, it will be appreciated that the elements may be present or may be positioned in locations other than illustrated in this schematic.

The system 100 may include at least one laser 110. In one embodiment, the laser 110 may be a diode laser or an optical parametric oscillator laser configured to operate in the near IR spectrum, having a wavelength between about 750 to 2,000 nm (0.75 to 2.0 µm).

Light from laser 110 is configured to operate at pre-selected optical frequencies which excite at least one overtone frequency, at least one combination band frequencies, or a combination thereof, of a sample 50 comprised of one or more of materials. The laser 110 may be a diode laser, for instance. Depending on desired operation, the laser 110 may be continuous or modulated at a fixed acoustic frequency, pulsed, tunable, or a combination thereof. Modulated lasers at a fixed frequency facilitate filtering of ambient acoustic noise. Pulsed lasers are advantageous when the desired wavelength is only attainable with non-linear optics; yet the power of the resulting acoustic response is spread out over many acoustic frequencies, and can be more difficult to separate from ambient noise. To capture the unique spectral fingerprint of a hazardous material, laser tunability is required to capture as much of the absorption spectrum as possible. A wave-generator 112 generates and outputs signals to a laser driver 114 which controls the laser 110. Laser 110 is configured to excite energetic residues of hazardous materials such as explosives that may be present on a surface.

In some embodiments, multiple light sources may be employed for the laser 110. For example, an array of diode lasers operated at different acoustic frequencies and emitting different optical wavelengths can be used to measure the material response to all the emitted laser wavelengths simultaneously. These are chosen based on a principle component analysis of near infrared spectra of the material to be detected and common substrate materials for maximum discrimination and sensitivity. Each laser element in the light source array may operate at a distinct optical wavelength and is also modulated at its own acoustic frequency, typically in the range of 5-20 kHz. This frequency range may be sufficient since environmental noise usually interferes at the lower acoustic frequencies. In one implementation, the lasers may be driven with square wave pulses and 50% duty cycle to create sinusoidal wave responses from absorbing substrates. To ensure easy filtering of the acoustic signal elicited from each laser element, it may be advantageous to ensure that there is adequate difference in modulation frequency between all the individual laser elements.

The beam 120 from the laser 110 may pass through optics 116 for directing (i.e., focusing) the directed beam 120' toward the target sample 50. For instance, the optics 116 may include one or more rotation beam scanners, lenses, beam combiners, beam windows, beam steering stages, collimators, or any combination thereof. Each laser beam may be focused to the same sampling area on the substrate that is being probed.

The sample 50 may include materials including one or more of: explosives, propellants, chemical warfare agents, hazardous materials, etc. In various implementations and uses of system 100, the detection and monitoring of energetic materials, such as 1,3,5-trinitrotoluene (TNT), 1,3,5-trinitro-1,3,5-triazacyclohexane (RDX), 2,4,6,8,10,12-hexanitro-2,4,6,8,10,12-hexaazoisowurtzitane (CL20), and other hazardous materials, such as chemical warfare and toxic industrial chemicals (TICS), may be important for various military and security interests. In addition, molecules containing methylidyne (CH), hydroxyl (OH), and/or nitrogen monohydride (N—H) components may be of particular importance, for example, since overtone absorptions for many moieties, such as, for example, those having C—H, O—H, and NH vibrations, fall in the near IR wavelength region. An appropriate selection of laser wavelengths should be made to obtain sufficient selectivity and adequately low false positive rates.

As shown, the sample 50 is depicted as a solid residue on a surface or substrate 55. Various surfaces 55 such as, for example, luggage, clothing, epidermises (skin), vehicles, and buildings, etc. may exist which include suspect materials. However, it will be appreciated that the sample 50 may be in various forms including those in a liquid phase including, aqueous solutions (e.g., in water or water-comprised solution) and non-aqueous solutions (e.g., formulated in peroxides), in a vapor phase (e.g., an aerosol), or in a solid phase (e.g., films, residues, powders, coatings, etc). In response to the sample being irradiated by light 120', the sample 50 is stimulated and excited. This may cause specific vibrations of chemical bonds in the material. For example, carbon to hydrogen (C—H), nitrogen to hydrogen (N—H), oxygen to hydrogen (O—H), phosphorus to hydrogen (P—H), phosphorus to oxygen (P=O), or other stretches, combination bands, and/or other vibrations involving two or more atoms may be excited in this manner. As each compound or its surrounding environment produces its own characteristic change in pressure, temperature, or other related thermodynamic parameter, various energetic molecules can be monitored and distinguished. These particular phenomena enhance the selectivity of the system.

This excitation causes the sample 50 to express a physical phenomenon 125, or multiple phenomena, in some cases. The physical phenomenon 125 may include, but is not limited to, a sample's change in pressure, temperature, density, refractive index, displacement, or changes in the sample's surrounding medium, such as air. If sufficient laser energy is absorbed by material on a surface, then a photoacoustic signal may occur. In this case, molecules of the sample 50 convert part of the absorbed radiation into heat which is transferred to the ambient air. The change in pressure of the air produces acoustic or sound waves which result from non-radiative and collisional processes. In some instance, these may be further enhanced at atmospheric pressure. Alternatively or additionally, one or more tunable lasers can be used to irradiate the sample and probe the induced change in temperature, induced surface displacement, or related phenomena of the sample or its environment.

These physical phenomena 125 can be measured and/or detected. Thus, a detector 130 is provided which is configured to measure or detect the physical phenomenon 125 of the sample 50 in response to excitation by the laser 110. While one detector 130 is illustrated in the figure, it will be appreciated that multiple detectors may be provided for measuring or detecting discrete phenomena.

In particular, spectral fingerprints of energetic materials are present in near-IR wavelength region. These fingerprints are different than those in the mid-infrared, and arise from overtone absorptions (e.g., absorption of light that takes a molecule from the ground vibrational state to an excited vibrational state) involving vibrations and/or combinations of these vibrations in the energetic materials. This may include the C—H bond stretching vibrations and/or others.

Photoacoustic absorption spectra for various energetic materials, including TNT, RDX, and CL20 at atmospheric pressure and temperature, show unique spectra to each measured material which can serve as a fingerprint for that material. In the case of CL20, for example, various polymorphs have been detected. Fingerprint information can be obtained with one or a few discrete wavelengths. Other materials are believed to have unique fingerprints and signatures which may be similarly detected and identified.

In the case of measuring or detecting photoacoustic phenomenon, the detector 130 may include a microphone to detect their emitted sound waves. The microphone may be a standard electret microphone that has a sufficient sensitivity, for instance. In some implementations, an acoustic mirror may be further provided which concentrates photoacoustic signals onto the microphone. For high frequencies (such as, e.g., 10-20 kHz), an acoustic mirror on the order of about 10 cm in diameter may be sufficient.

Alternatively or additionally, the detector 130 may include other detectors to monitor the temperature or other thermodynamic property of the sample or its environment, and changes thereof. For example, the detector 130 may be configured to measure or detect: (a) a change in pressure in the sample and/or its environment; (b) a change in temperature in the sample and/or its environment; (c) a change in the displacement of the sample and/or its environment; (d) a change in index of refraction in the sample and/or its environment; (e) a change in reflectivity in the sample and/or its environment; and/or (f) a change in light emission from the sample and/or environment. In some embodiments, the detector may have the capability of detecting change in pressure of the sample's environment (e.g., in this case air, but should work for aqueous and other environments) by using a microphone (see, e.g., FIGS. 8A and 8B), and have the capability to measure sample displacement using piezoelectric film or laser interferometer (see, e.g., FIGS. 9A and 9B). The sample temperature may be measured by optical or infrared pyrometry using a probe laser, and the sample's surrounding air temperature may be measured by laser Raman scattering of nitrogen ($N_2$). In the latter case, the probe laser may be tuned to various $N_2$ ro-vibrational transitions and the temperature calculated from the change in the Boltzmann distribution of the $N_2$ molecules. The index of refraction may be measured by laser interferometry (see, e.g., FIG. 9A), or by a laser-based system such as the one described in U.S. patent application Ser. No. 13/292,379, herein incorporated by reference.

Because an acoustic signal is generally inversely proportional to the square of the distance between the sample and the microphone, the detector 130 may be spaced from the sample 50 by a relatively small non-contact distance, e.g., on the order of centimeters, for a high signal-to-noise (S/N) ratio. On the other hand, where pressure, temperature, index of refraction, reflectivity, and/or other phenomenon, of the sample or its environment are being monitored, the system 100 may positioned near or far from the sample 50. In these cases, the system 100 may be positioned remotely from the sample 50 by a relatively large non-contact distance, e.g., on the order of tens of meters or even more. In the case of optical signals, the received physical phenomena 125 as light may pass through optics 132 for directing (i.e., focusing) the directed light 125' toward the detector 130. For example, a laser vibrometer may be used in place of a standard acoustic microphone. An advantage to this approach is that only displacement on the sample surface is detected. Thus, pressure waves originating from the air in the pathlength of the excitation laser from vapor, especially water vapor, cannot contribute to the detected signal. An added benefit is that this arrangement does not suffer from signal loss at the surface interface with the air. Additionally, it becomes possible to access acoustic ultrasound frequencies (e.g., f>100 kHz), where there is little acoustic noise.

The physical phenomena 125 may be detected, amplified with a standard amplifier circuit, and/or filtered before, during or after being measured or detected by the detector 130. It may be digitized using an analog to digital converter so that there is a signal strength number associated with each laser's operating wavelength. The signals whether originating from a microphone or other detectors may be fed into an amplifier 134 connected to a frequency filter 136. An analog-to-digital (A/D) converter may also be provided to digitize the output signals, which are then fed to an analyzer 140.

The analyzer 140 is configured to analyze the detected physical phenomenon measured or detected by the detector 130 and to identify the one or more materials corresponding to that of the sample 50. In some embodiments, the identification may be based on comparison of the detected physical phenomenon with known signatures of one or more materials. A Fourier analysis or other regression analysis and/or principal component analyses may be used for identification in various embodiments. The analyzer 140 may be a computer or microprocessor, for example, for processing.

A database 150 may comprise one or more electronic databases which store known signature for various materials. Database 150 may be a rational database, for example. Various material signatures may be stored as electronic records in the database 150. The database 150 may be coupled to the analyzer 140. In some implementation, the database 150 may be remote to the analyzer and communicate thereto through a network 155, such as, for example, the Internet, intranet, or other network. Alternatively or additionally, the system 100 may include a database or memory incorporated into the housing 105 which can perform a similar function. Also, past detected signatures may be stored in database 150 for further analysis and/or future searching in some instances.

A display device 160 is configured to display information, such as one or more "best" matches determined by the analyzer 140 for the sample 50. The display device 160 may include any known display device, such as, a liquid crystal display (LCD), cathode ray tube (CRT), plasma display, etc.

In addition, the system 100 may include a warning device 170 that is configured to provide a warning when certain materials, such as, toxic materials or chemical agents, are detected. This may be instrumental, for instance, in the case of attack chemical warfare agents, so that personnel can begin to take protective actions. The warning device 170 may include an audible alarm or siren, flashing or strobe light, display screen, etc. which can provide audible and/or visual warnings. In some instances, written instructions may be provided by the display device 160 or a printer for the aid of personnel. If the system 100 is connected to a network (e.g., phone, Internet, intranet, etc.), it may generate messages to contact first responders or other emergency personnel, command and/or other persons, as desired.

Figure 2B:
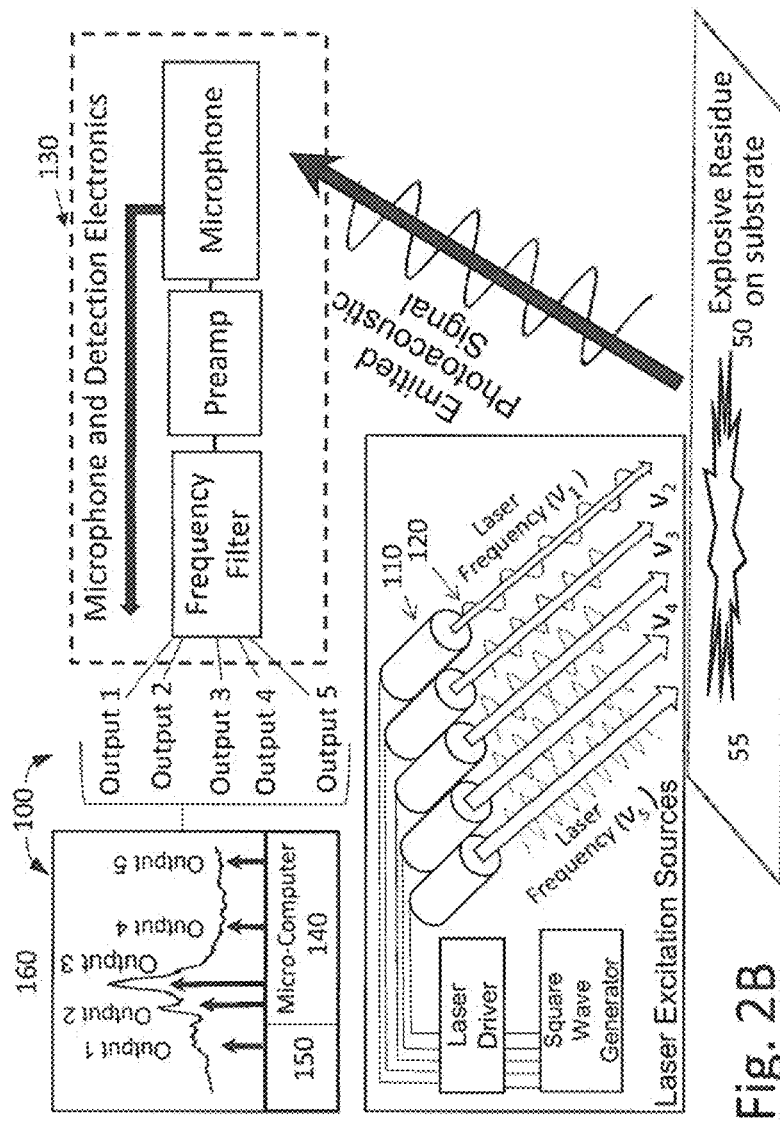
Figure 2C:
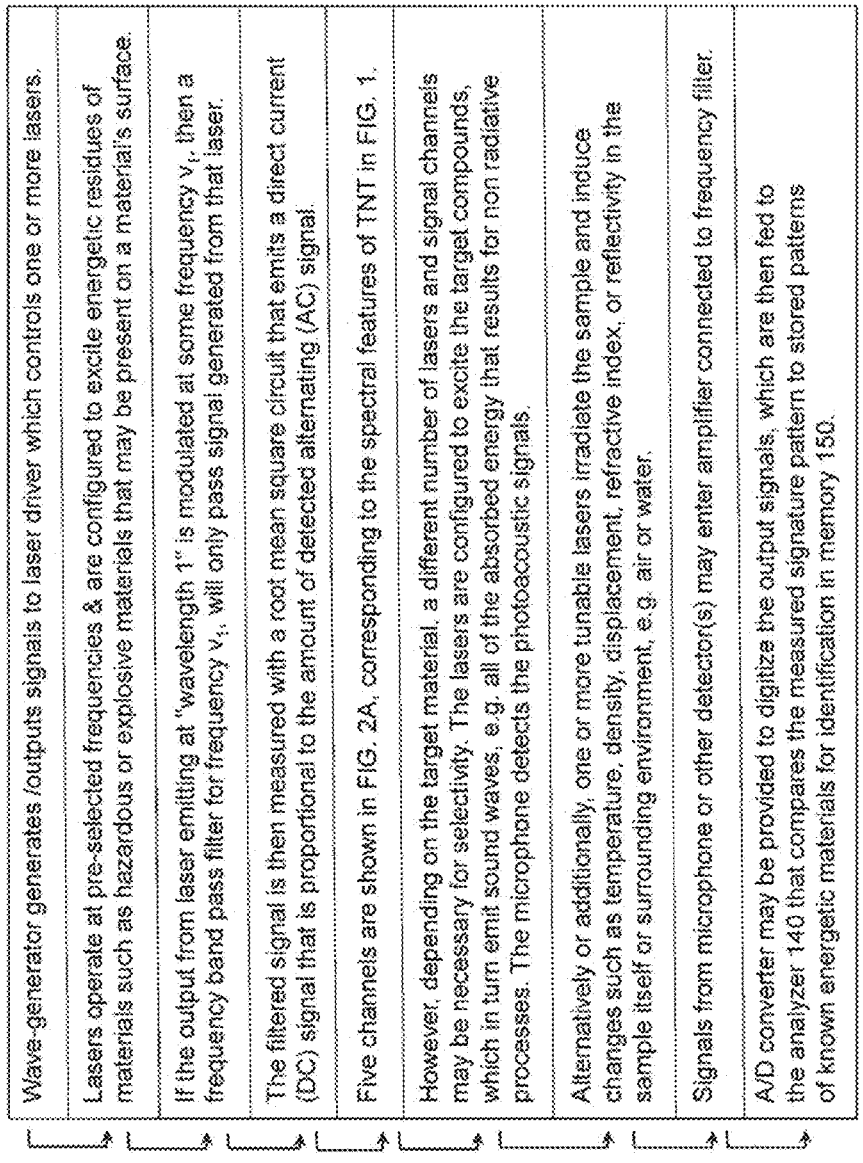
FIG. 2C is a flow chart of a method for detection materials according to an embodiment.

FIG. 2B is a schematic diagram of a method for detection materials according to an embodiment of the present invention. The method may implemented using the system illustrated in FIG. 2A, with flow chart in FIG. 2C, having multiple lasers in some implementations.

The method may be practiced in the following manner. The wave-generator generates and outputs signals to a laser driver which controls one or more lasers. Here, as shown, there may be an array of five lasers. These lasers, which operate at pre-selected frequencies, are configured to excite energetic residues including at least one vibrational overtone frequency, at least one combination band frequency, or a combination thereof, of materials such as hazardous or explosive materials that may be present on a material's surface.

For example, as shown in this figure, if the output from laser emitting at "wavelength 1" is modulated at some frequency $v_1$, then a frequency band pass filter for frequency $v_1$, will only pass signal generated from that laser. The laser may be configured to output IR light, and more particularly, light in the near infrared (IR) spectrum, in some embodiments. The filtered signal is then measured with a root mean square circuit that emits a direct current (DC) signal that is proportional to the amount of detected alternating (AC) signal. Five channels are shown in this figure, corresponding to the spectral features of TNT in FIG. 1. However, depending on the target material, a different number of lasers and signal channels may be necessary for selectivity. The lasers are configured to excite the target compounds, which in turn emit sound waves, e.g. all of the absorbed energy that results for non radiative processes. The microphone detects the photoacoustic signals.

Alternatively or additionally, one or more tunable lasers irradiate the sample and induce changes such as temperature, density, displacement, refractive index, or reflectivity in the sample itself or surrounding environment, e.g. air or water. These changes are monitored with appropriate detectors. The signals whether originating from a microphone or other detectors are fed into an amplifier connected to a frequency filter. An analog-to-digital (A/D) converter may be provided to digitize the output signals, which are then fed to the analyzer 140 that compares the measured signature pattern to stored patterns of known energetic materials for identification.

Figure 3:
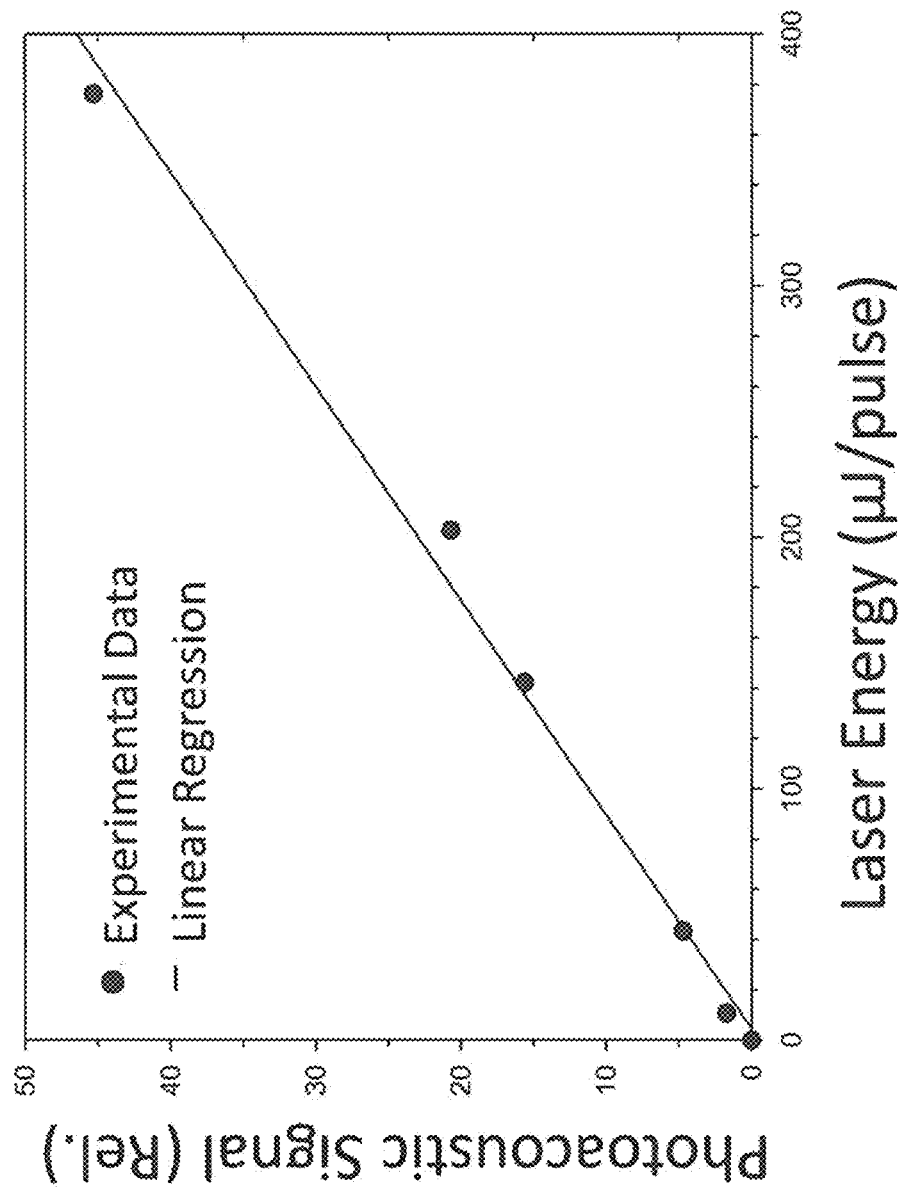
FIG. 3 illustrates TNT signals as a function of laser energy.

FIG. 3 shows a plot of the photoacoustic signal intensity as a function of laser energy near 6080 cm$^{-1}$ for TNT. Part of the pulsed laser energy absorbed by TNT is converted into heat. The rapid local heating and cooling of the sample and its surrounding gas causes a change in pressure that generates acoustic waves. The signal amplitude depends linearly on the energy absorbed by the sample, the absorption coefficient of the sample, the sample's thermal diffusivity, and the interface coupling between the sample surface and its surrounding gas. FIG. 3 shows that signal varies linearly with laser energy in the range from about 10 to 400 microjoules. The signal is not saturated and an increase in laser energy will increase the sensor's sensitivity.

Figure 4:
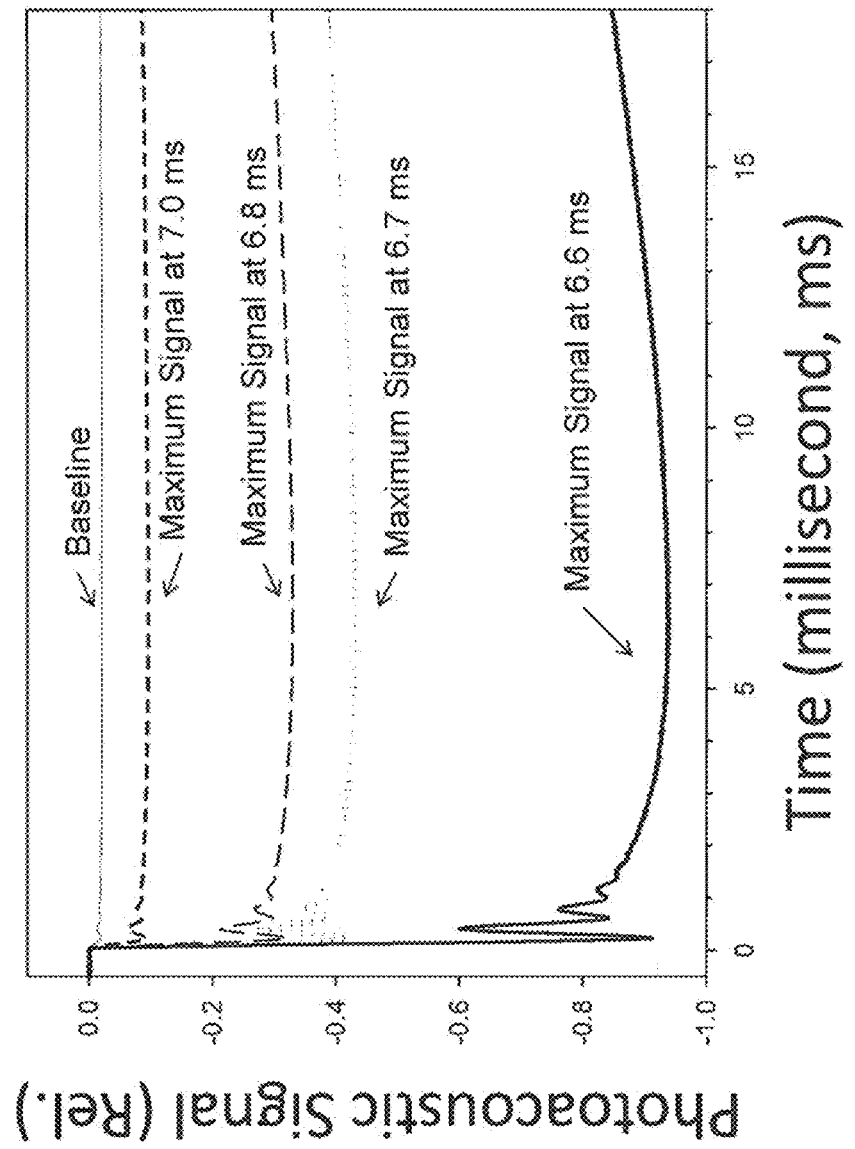
FIG. 4 illustrates signal-time waveforms of TNT at various laser energies.

FIG. 4 shows TNT wave traces with increasing laser energy. The shape of the wave traces is indicative of the thermal properties of TNT relative to the ambient gas. The fast rising and falling initial signal is present without sample and is due to absorption by the cell itself. The slower rising component of the signal is only observed when the sample is present in the cell and the laser wavelength is tuned to an absorption feature. The time delay from the laser pulse to maximum acoustic signal decreases somewhat at the higher laser powers, increasing from 6.6 ms at 377 µJ/pulse to 7.0 ms at 44 µJ/pulse. The total time delay arises because the thermal diffusivity of the sample TNT governs the flow of heat from the sample into the surrounding gas.

Previously, Rosencwaig and Gersho solved the one dimensional, heat flow equations from a solid sample into a gas. See A. Rosencwaig and A. Gersho, "Theory of the photoacoustic effect with solids." *J. Appl. Phys.*, 47(1), 64 (1976), herein incorporated by reference. They found that the thermal diffusion length, µ, limits the depth within the sample that can contribute to the acoustic signal. Although their model treats the laser heating as a sinusoidal function, the expression for the thermal diffusion length is still valid for a pulsed laser, and is given by the following equation:

$$\mu = \left(\frac{f\rho C}{4\pi k}\right)^{-1/2} \quad (1)$$

where f is the chopping frequency of the incident laser light, ρ is the solid sample density (1.6 g/cm$^3$ for TNT), C is the sample specific heat (2.1 J/g/K for TNT), and k is the sample thermal diffusivity constant ($2.15 \times 10^{-3}$ J/s/K/cm for TNT) according to A. Rubenchik, "On the Initiation of High Explosives by Laser Radiation," *Propellants, Explosives, Pyrotechnics*, 32(4), 296 (2007), herein incorporated by reference.

The thermal diffusion length depends on the time for heat to escape from the interior of the sample into the surrounding gas. The time delay shown in FIG. 4 is a reflection of the heat diffusion from the interior of the sample to the surface. Using the inverse of the time delay (e.g., 6.6 ms) for the chopping frequency and equation 1, a characteristic thermal diffusion length of 72.8 µm is determined. Although the input laser power varied by nearly a factor of ten, the time delay between the laser pulse and the maximum acoustic signal only increases by about 10%. This suggests that the spatial gradient of the thermal distribution function determines the rate of heat flow. Because the laser pulsed heating is practically instantaneous, the temperature gradient is very high for each laser pulse, the energy that is used in this measurement, and the delay time changes little. Given that there is no signal saturation due to laser power, and that the signal delay does not decrease significantly when the laser pulse energy is increased, the thermal diffusivity of the sample drives the signal delay time. For photoacoustic measurements of sample films of known thermal properties, the delay time could be used as a measurement for sample depth.

Figure 5B:
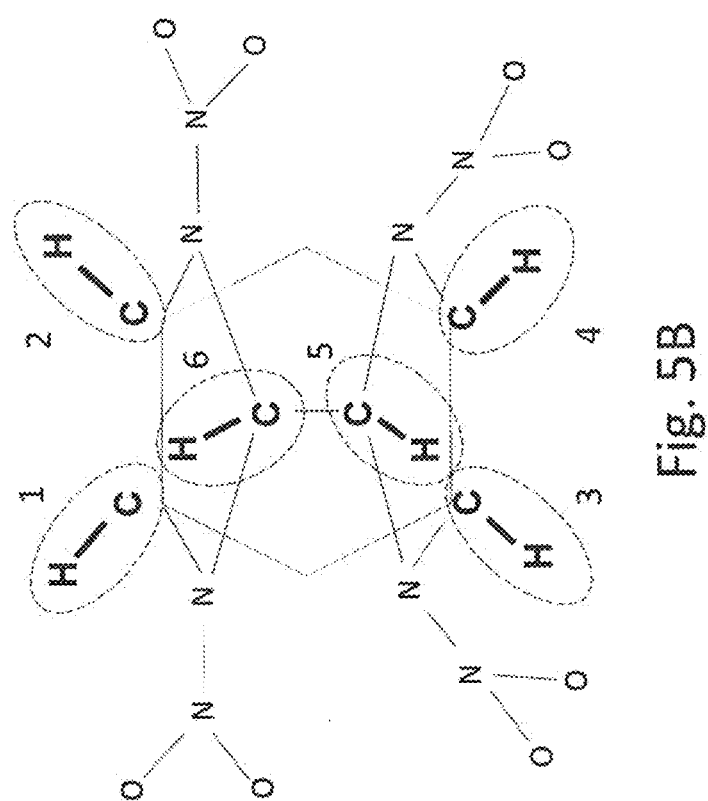
FIG. 5B schematically illustrates the C—H position numbering of CL20.
Figure 6:
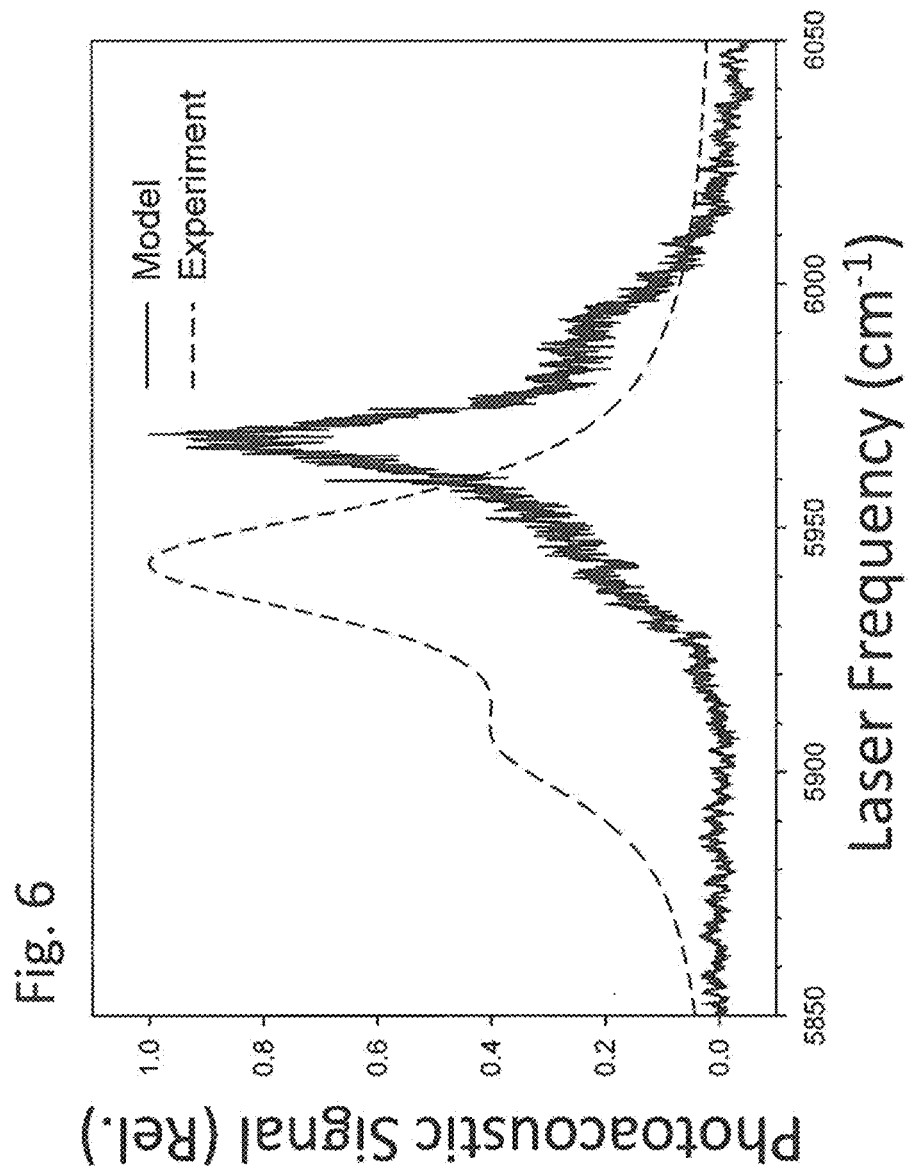
FIG. 6 illustrates calculated and observed spectra of beta CL20 in the near IR spectrum.

FIG. 5A shows quantum mechanical calculations for the various polymorphs of CL20 at ambient pressure and temperature. Polymorphs are identical chemical compounds having different crystal structures. Each polymorph, i.e., alpha, beta, epsilon, or zeta, has 6 characteristic peaks resulting from the 6 C—H vibrations that vary in intensity and frequency. The distinct spectra thus allow for their identification. FIG. 5B shows the C—H oscillator position numbering for the CL20 alpha polymorph FIG. 6 shows calculated and observed spectra of beta CL20 in the near infrared (NIR) spectra. Overall, the model predicts the experimental spectra well, with about a 30 cm$^{-1}$ difference between calculated and observed main peaks.

FIGS. 7-9 illustrate various other systems for detecting materials according to embodiments of the present invention.

Figure 7A:
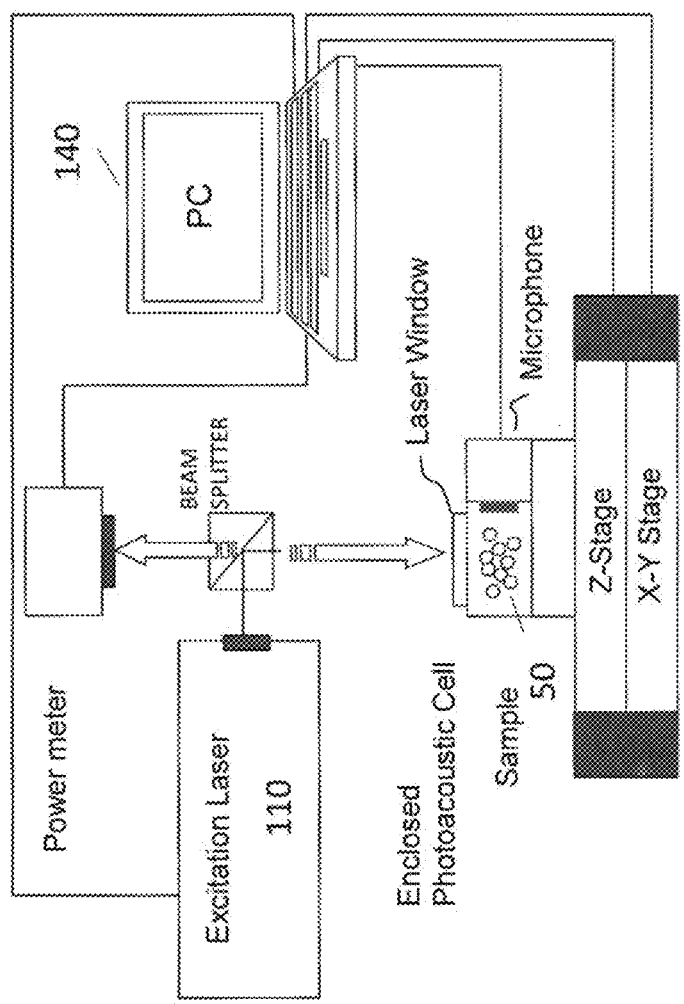
FIG. 7A is a schematic illustration of a material detection system comprising a microphone detector according to an embodiment.
Figure 7B:
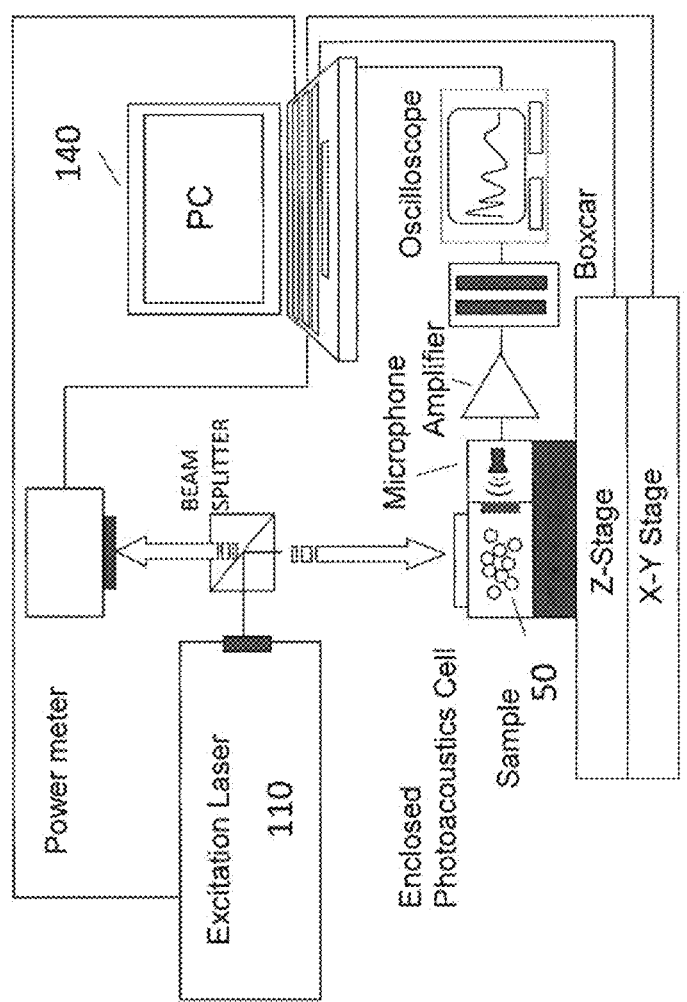
FIG. 7B is a schematic illustration of a material detection system connected to an oscilloscope according to an embodiment.

FIG. 7A illustrates a material detection system according to an embodiment of the present invention. This system was used by inventors for conducting experiments. Here, the system employs a tunable, pulsed excitation laser 100, a photoacoustic cell which includes a microphone for detection of photoacoustic signatures and a computer 140 configured for identifying "matches" of known materials which best correspond to the detected photoacoustic signatures for a sample 50. For the experiments conducted by the inventors, samples were placed inside the cell and the laser is tuned in the range of 1.65 to 1.75 µm. FIG. 7B is a schematic illustration of a material detection system connected to a boxcar signal integrator and an oscilloscope according to an embodiment.

FIGS. 8A and 8B illustrates illustrate two remote material detection systems according to embodiments of the present invention. The systems may be a stand-alone apparatus or mounted to a platform, such as a robot. In FIGS. 8A and 8B, the suspect material is depicted as being a residue on a suitcase or luggage 801 having an energetic material 802 therein. The sensor 803 is depicted in FIG. 8A wherein the laser-induced acoustic signal is reflected and/or collimated by a reflector 804 into a microphone 805. The signal from the microphone 805 passes through an amplifier 806 into a filter 807 for processing by a microcomputer 808. The results may optionally be displayed on a display 809. Also shown in FIG. 8A are laser pointers 810 of different wavelengths for probing the target overtone and/or combination transitions of suspect materials. The laser driver 811 may be driven by a square wave generator 812. These systems employ a tunable excitation laser, a microphone for detection of photoacoustic signatures and microprocessor configured for identifying matches of one or more known materials which best correspond to the detected photoacoustic signatures. In FIG. 8A, the system is configured as a unitary apparatus, whereas in FIG. 8B a flexible hand-held detector arrangement is provided which includes the microphone. FIG. 8B comprises a tunable laser 850 operatively associated with a fiber optic cable 852. The stand-off distance (i.e., distance between the system and suspect material) may range from a few centimeters to meters.

Figure 9B:
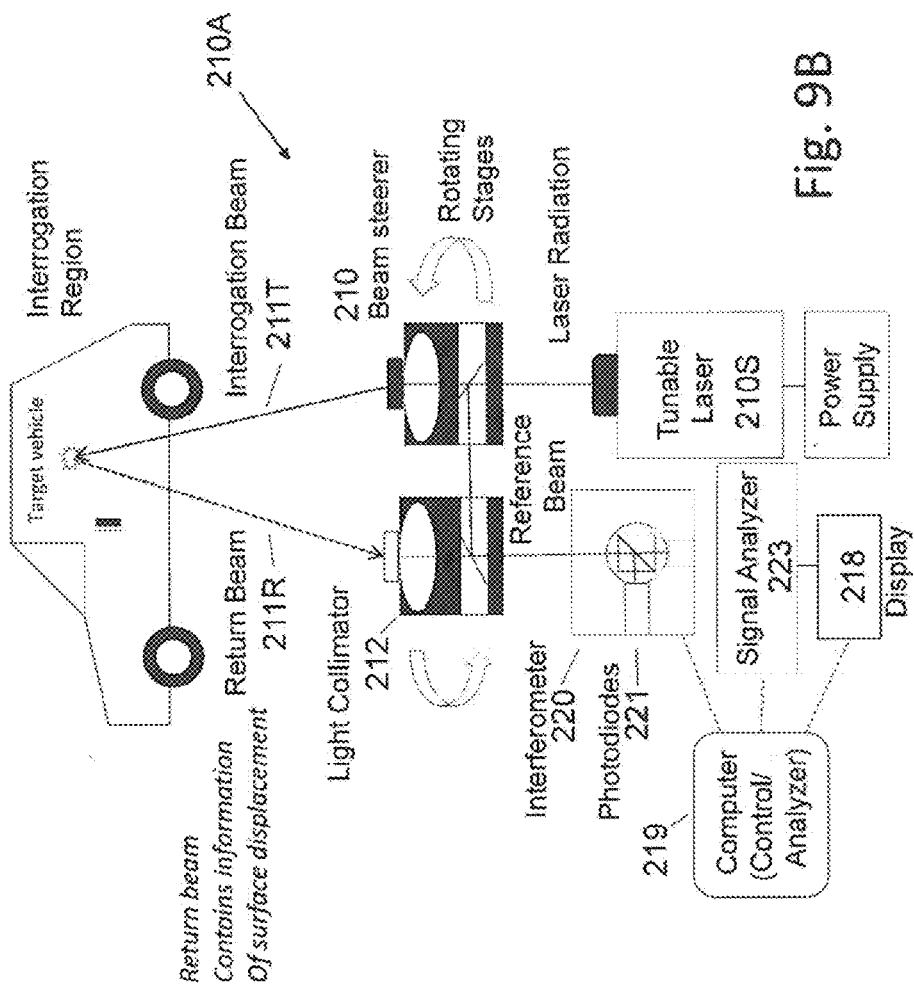
FIG. 9B is a schematic illustration of a material detection system capable of vehicular usage by probing the displacement of the material's surface or vibration using laser vibrometer according to an embodiment.

FIGS. 9A and 9B illustrate two remote material detection systems according to embodiments of the present invention. Here, the suspect material is depicted as being a residue on a vehicle 201, such as an automobile. The embodiments depicted schematically in FIGS. 9A and 9B employ a tunable excitation laser 110. The radiation from laser 110 may optionally enter a beam scanner 210S or beam steerer 210 having rotating stages. In FIG. 9A, the beam scanner 210S transmits an interrogation beam 211T by which both wavelength and position are scanned. The return beam 211R contains information relating to sample 201S after absorbing interrogation beam 201T. Instead of detecting and measuring photoacoustic signatures with a standard microphone, though, these systems include sensors to detect laser absorption and/or displacement or vibration of the surface of the sample. This system essentially incorporates a laser vibrometer in place of a standard microphone to detect material response at a given excitation laser wavelength. This system includes a microprocessor configured for matching recorded spectra to a database of absorption spectra of threat materials. The stand-off distance may be tens of meters or more. FIG. 9A illustrates the interrogation beam and return beam being generally coaxial to one another. This system uses a piezoelectric film based sensor 213 in which current or voltage is induced on the film by the return beam to determine laser absorption by the sample or an interferometer 220 to determine displacement of the piezoelectric film. Thus, the embodiment shown in FIG. 9A may optionally measure piezoelectric film in sensor 213 induced current electronically or its displacement by interferometry using inferometer 220. The assembly further comprises mini-laser 215, current amplifier 216 and oscilloscope 217 connected to a display 218. FIG. 9B illustrates the interrogation beam and return beam being physically separate. In FIG. 9B, the beam steerer 210 directs an interrogation beam 211T. The return beam 211R contains information relating to surface displacement. The return beam 211R passes through a collimator 212. An interferometer 220 with photodiodes 221 detects the return beam and can determine the surface displacement of the sample. A signature analyzer 223 may be utilized and connected to an optional display 218 interfaced to computer control and analyzer 219. Optionally, using beam splitters in connection with both the collimator 212 and beam steerer 210, a reference beam may be transmitted there between as shown in FIG. 9B.

Regarding FIGS. 8A and 8B, the laser 811 operating in the near IR spectral region irradiates the target material. In FIG. 8A, the microphone is the detector and the whole unit is the sensor. The sensor head in FIG. 8B comprises all the elements in FIG. 8A except for the laser pointers and associated electronics (drivers and square wave generator); the laser pointers being replaced with a tunable near IR laser. If the laser frequency is resonant with a frequency associated with the materials' overtone energetic material 802 and/or combination band transitions, then the material 802 will absorb the laser energy. There are many pathways for the material to dissipate this energy, including fluorescence, ionization, and photoacoustic. The photoacoustic channel (including microphone 805) operates using non-radiative processes. If the absorbed energy is converted into heat, then it may be transferred to the ambient air. The pressure fluctuation caused by the rapid heating and cooling appears as compression and rarefaction of the air and results in sound waves, which can be detected by a microphone 805, for example. In addition to pressure fluctuations, one may monitor the materials change in temperature, volume, index of refraction, surface displacement, etc. or changes in the material's environment. Different molecules or molecules with the same molecular formula, but different molecular structure have unique overtone and/or combination transitions (fingerprints) and thus produce distinct sounds (or other observables) characteristic of that material. In the case of pressure fluctuations, the characteristic sound signals decrease with distance. Thus, it would be preferable to have the sensor 803 (FIG. 8B) in close proximity to the object under investigation with suspect material 805. FIG. 8A shows a miniature sensor 803 that can be mounted on a robot for hostile conditions or can be used as a hand-held sensor for friendly environments. Note that FIG. 8A shows multiple, small laser pointers 810 with output radiation at a single frequency to achieve the resonance condition for target materials. Optionally, a tunable IR laser could be utilized; tunable to many frequencies and thus probe many types of compounds, e.g. energetic materials, chemical warfare (cw) agents, industrial wastes etc. However, generally such lasers are of limited availability in sizes as small as single frequency laser pointers 810 at the present time. However, one can set the tunable near IR laser on a table or vehicle, which can be located tens of meters from the object under investigation, and use a fiber optic to transmit the beam close to the object (FIG. 8B). The sensor head 854 capturing the sound can be made very compact and light so that an individual or robot (not shown) can easily maneuver it.

Figure 9C:
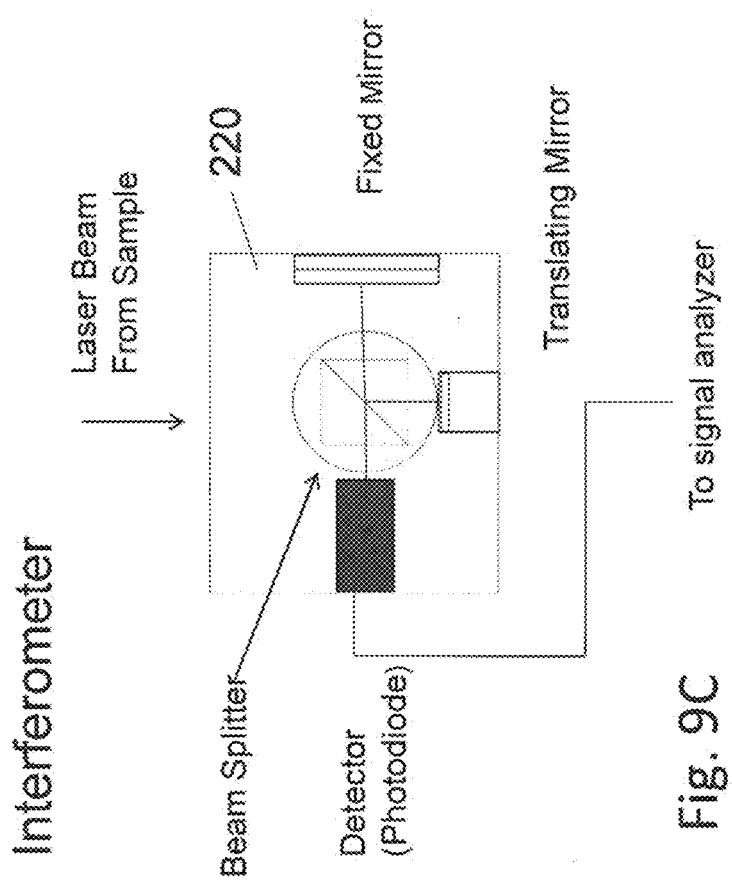
FIG. 9C is a schematic illustration of the interferometer shown in FIG. 9B.

Probing the material's laser-induced sound waves may only work for remote detection at close distances. Distances of meters to tens of meters require more sensitive equipment because the laser-induced sound decreases with distance. In such cases it would preferable to use a near IR laser for irradiation, as described above, and the same laser to monitor the material's vibration or surface displacement using a laser-type vibrometer (FIG. 9B) or piezoelectric film based sensor 213 near the transmitted laser source and monitor the displacement of the film with an interferometer (FIGS. 9B and 9C). It is noted that both FIGS. 9A and 9B show the use of one laser to both excite and probe the material. However, optionally, one can use an IR tunable laser to irradiate the sample and a second laser with output in the ultraviolet, visible, or infrared to monitor the surface displacement or vibration of the material in question.

Both of the embodiments shown in FIGS. 9A and 9B may comprise computer (control analyzer) 219. The stand-off distance may range from a few centimeters to meters.

Overtone Spectroscopy

Laser-based sensors offer high sensitivity and species selectivity with real-time capabilities for monitoring the vapors of some energetic materials. However, the extremely low vapor pressure of many solid energetic materials under ambient conditions impedes these sensors. A preferred embodiment utilizes a novel technique based on laser photoacoustic overtone spectroscopy to detect and differentiate solid 1,3,5-trinitrotoluene (TNT), 1,3,5-trinitro-1,3,5-triazacyclohexane (RDX), and 2,4,6,8,10,12-hexanitro-2,4,6,8,10,12-hexaazaisowurtzitane (CL-20) in real time at ambient conditions. A tunable, near-infrared laser excites the target compound in the spectral region between 5800 to 6100 $cm^{-1}$, and a microphone monitors the sound that they generate by non-radiative, collisional deexcitation processes. The photoacoustic signals result from first-overtone and combination absorptions of the energetic material's C—H vibrations, and the collisional processes enhance the signal at atmospheric pressure. The spectra reveal features that are unique to each measured material and these features can serve as a fingerprint for that material.

Figure 10:
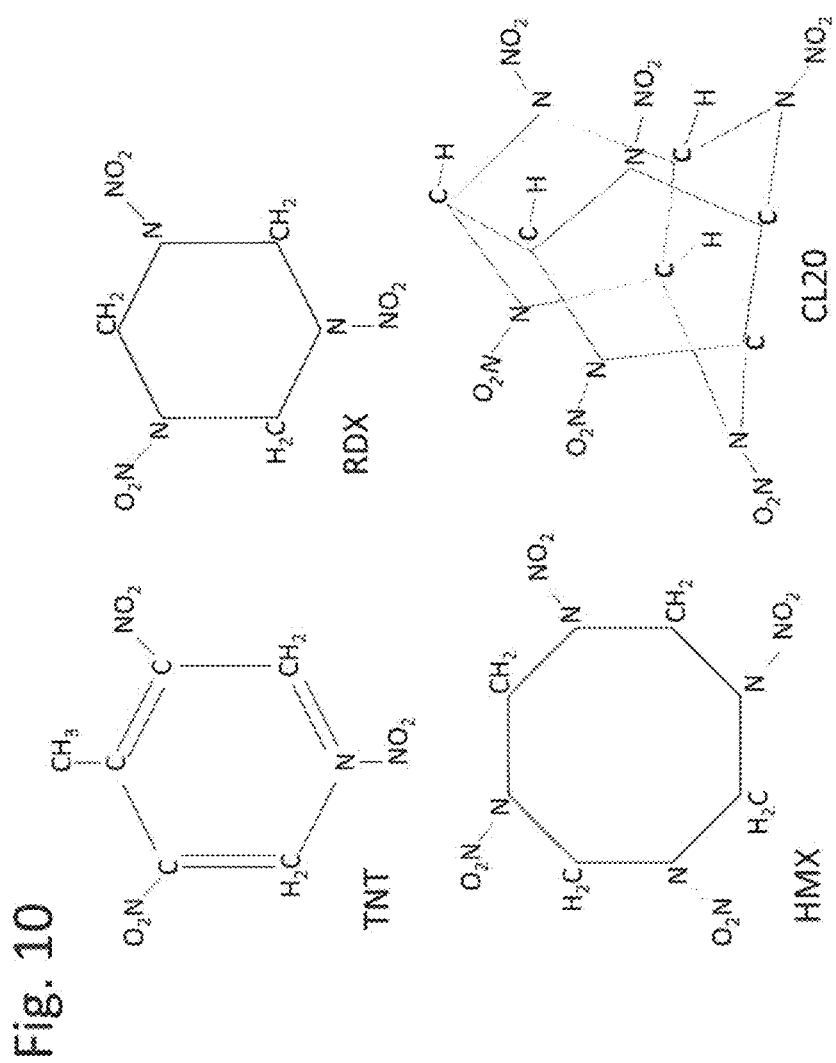
FIG. 10 is an Illustration showing structural formulas of selected energetic materials.

The detection and monitoring of energetic materials in real time at ambient conditions is important in many areas, including the detection of potential terrorist activity, demilitarization, and forensics, and it presents a technological task of increasing significance. A real-time device that is sensitive, accurate, robust, and detects these materials without sample preparation and under ambient conditions would be invaluable in both military and civilian applications. As a result of interest in these areas, numerous devices have been developed to reduce the risk to the general population and military personnel. Moore (D. Moore. "Instrumentation for trace detection of high explosives" Rev. Sci. Instrum. 2004. 75(8): 2499-2512) provides a critical and comprehensive review on instrumentation for detecting high explosives. Ion mobility spectrometry (IMS) is the current state of the art for sensing vapors and is commonly in use in airports and other secured areas. IMS has typical detection limits on the order of 1-10 ppb. However, its application for detecting solid explosives without sample preparation in real time is limited, as are other conventional sensors that use detectors to sense vapors, because many energetic materials have a low vapor pressure under ambient conditions (see FIG. 10 for the structural formulas of selected energetic materials). For example, 1,3,5-trinitro-1,3,5-triazacyclohexane (RDX) has a vapor pressure of $5 \times 10^{-9}$ torr or 7 ppt at ambient conditions, three orders of magnitude less than 1,3,5-trinitrotoluene (TNT). RDX's vapor pressure is still higher than the vapor pressure of many other relevant energetic materials, including 2,4,6,8,10,12-hexanitro-2,4,6,8,10,12-hexaazaisowurtzitane (CL-20). An added complication for gas-phase sensors is that vapor molecules of energetic materials tend to readily adsorb to surfaces, further reducing molecules available for detection.

Laser-based techniques offer both in-situ and remote monitoring capabilities with high sensitivity and species selectivity for analyzing many different solid energetic materials in real time. Some of these techniques include laser-induced breakdown spectroscopy (LIBS), laser photofragmentation-fragment detection (LP-FD) spectroscopy, Raman spectroscopy, and Terahertz spectroscopy. LIBS and LP-FD offer indirect detection of energetic materials on surfaces, whereas Raman spectroscopy and Terahertz spectroscopy directly detect the materials. In LIBS, a high-powered, focused laser beam completely breaks down the complex energetic material into its constituent elements, which are then detected by emission spectroscopy in the ultraviolet or visible spectral region. In contrast, LP-FD breaks down the complex explosive molecule into larger fragments or signature molecular groups such as $NO_2$ and NO that are detected subsequently by laser-induced fluorescence (LIF) and/or resonance-enhanced multiphoton ionization (REMPI), thus indicating the presence of the energetic material. Both LIBS and PF-FD detect energetic materials indirectly because they do not identify the target materials. Instead, they identify characteristic fragments resulting from the photolysis or decomposition of the energetic materials. As a result, the selectivity of these methods is not as high as those that involve direct detection. Also, trace quantities of atmospheric $NO_2$ may interfere with the measurements.

Raman spectroscopy and Terahertz spectroscopy have proven successful for directly detecting energetic materials in the condensed phase with chemical specificity. Terahertz spectroscopy has the additional advantage that it allows for the detection of concealed explosives because the radiation penetrates visibly opaque materials, such as clothing, paper, and plastics. Raman spectroscopy uses visible or ultraviolet radiation to probe the molecule's vibrational and rotational states from the inelastic scatter of photons, whereas Terahertz spectroscopy uses radiation in the range of 0.1 to 10 THz (1 THz=33.33 $cm^{-1}$) to probe the molecule's collective, internal vibrations or intermolecular crystal lattice vibrations, known as phonon modes. Although both techniques show great promise for energetic material detection, they face certain challenges. Raman spectroscopy suffers from weak signals without ultraviolet resonance or surface enhancement and Terahertz spectroscopy suffers from attenuation by water vapor in the atmosphere. Also, Terahertz spectroscopy suffers from the relative weakness of the spectral features in reflection and the limited frequency range available for detecting concealed explosives because of absorption by clothing or other materials. However, imaging at frequencies less than 1 THz shows more promise for security applications, although not offering the same specificity as the higher frequencies. Laser photoacoustic spectroscopy provides an alternate means of directly detecting solid energetic materials. In A. Bell. "Upon the production of sound by radiant energy". Paper read at National Academy of Sciences, Apr. 21, 1881, Washington D.C.: Gibson Brothers Printers, 1881, Bell reported the photoacoustic effect when he found that materials emit sound when exposed to a rapidly interrupted sunlight beam. The sample converts the absorbed laser radiation into heat by non-radiative, de-excitation processes. Ambient air absorbs this heat and the rapid sample heating and cooling causes a pressure fluctuation. The compression and rarefaction of the air results in a photoacoustic wave or sound that can be monitored with a microphone or laser vibrometer. Unlike most optically based detection methods, photoacoustic methods are highly insensitive to light scattering by substrates and are only sensitive to actual absorption of optical radiation.

The advent of lasers spawned a new era in photoacoustic spectroscopy because their output radiation is spatially and temporally coherent, high in energy, and spectrally tunable. Despite the copious number of papers published on the photoacoustic detection of materials, only a few papers center on the laser photoacoustic spectroscopy of solid energetic materials by monitoring their sound emissions. Spectral fingerprints of energetic materials are ubiquitous throughout the infrared (IR) spectral region. These fingerprints result from a molecule's stretching and bending modes and arise from fundamental vibrational absorptions (absorption of light from a molecule's ground vibrational state to the first excited vibrational state, $v=0$ to $v=1$ transitions). The resulting features are sharp and well-resolved compared to those that result from a molecule's electronic absorptions in the ultraviolet or visible spectral region.

Energetic materials possess spectral fingerprints in the 3 to 4 lm spectral region in addition to those in the region from 9.6 to 10.6 μm. These fingerprints arise from the energetic material's fundamental C—H vibrations. However, bright laser sources are not widely available in this region. Interband cascade lasers are promising light sources in this region, but they have not reached the same maturity as $CO_2$ lasers or quantum cascade lasers (5-12 μm). Bright laser sources are available, however, in the spectral region 1.5 to 2.0 μm. In this region, the radiation energy is resonant with the energetic material's first overtone CH stretching transitions, $v=0$ to $v=2$. Although the absorption cross-sections of the overtones are typically an order of magnitude less than the fundamental absorption, there are several advantages of using the overtone absorption bands of energetic materials. First, the availability of laser sources with very high output in this spectral region more than compensates for the relatively weaker overtone absorptions compared to the fundamental absorptions. Second, this region does not suffer from the interference from water vapor as much as other IR regions. This attribute is particularly important for remote sensing of energetic materials by laser photoacoustic spectroscopy by monitoring their emitted sound waves or changes in their temperature, reflectivity, or displacement. Third, some molecules may exhibit spectral features due to combination bands near the overtone bands, thus increasing the spectral selectivity of the laser-based detection technique. Lastly, this spectral region is "eye-safe" because it offers the highest protection to the laser operator or bystander compared to other laser spectral regions. Laser wavelengths shorter than this region cause damage to the eye's retina, whereas longer wavelengths cause more damage to the cornea.

Embodiments of the present invention provide a novel technique based on photoacoustic overtone spectroscopy to detect, for example, RDX, TNT, and CL-20 in the condensed phase in real time under ambient conditions. A laser excites the target compounds in the 1.6 to 1.8 μm spectral region (6250-5555 $cm^{-1}$) and a microphone detects the subsequent sound resulting from non-radiative processes. The spectral fingerprints of energetic materials originate from the first-overtone absorption of the various C—H stretching modes in the energetic materials. These features are different within both the sample molecule and different molecules. Thus, each molecule has its unique "fingerprint" that allows its identification.

Figure 11:
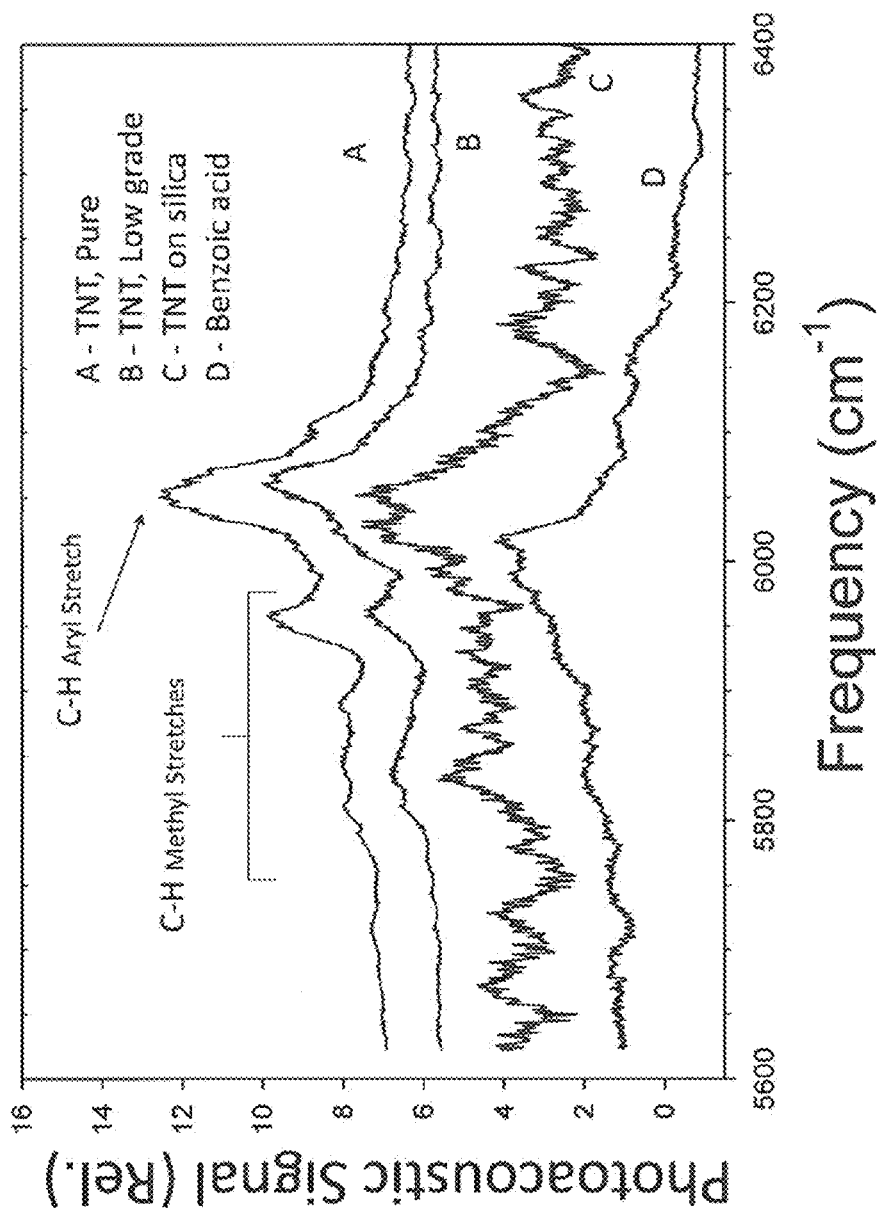
FIG. 11 is an illustration showing near-IR laser photoacoustic spectra of pure, recrystallized TNT, munition grade TNT, TNT deposited with solvent on fumed silica powder, and benzoic acid in the frequency range of 5700-6700 $cm^{-1}$.

As shown in FIG. 11, both pure and munitions grade TNT spectra show the same features at 5811, 5865, and 5956 $cm^{-1}$ and the shoulders at 6010 and 6095 $cm^{-1}$. There is a small shift in the strongest feature from 6051 to 6063 $cm^{-1}$ and a reduction in intensity for the 5880 $cm^{-1}$ peak when going from pure TNT to the munitions grade TNT. For the TNT adsorbed onto silica, there are two strong features centered at 6039 and 5860 $cm^{-1}$. Most notably, there is the absence of the peak at 5956 $cm^{-1}$, which is present in the munitions grade and pure TNT. The spectrum of benzoic acid is distinguishable from TNT, although there is a similar dominant feature that is red-shifted to 6016 $cm^{-1}$, with no additional distinct features in the spectrum. The simulations of overtone spectra using single molecules, an 8 molecule cluster, and 64 molecule clusters (eight unit crystal cells) have elucidated three key findings on the effect of intermolecular interactions on the overtone spectrum. First, the simulations showed that the crystal structure in the classical layer of the model was critical. Second, electron correlation must be accounted for to correctly capture third-order force constants for the C—H stretches. Finally, intermolecular forces must be accounted for by correct assignment of partial electric charge in both the quantum and classical layers of the model. The results of the single, 8, and 64 molecule cluster models illustrate how sensitive the simulated overtone spectra are to molecular placement. Single molecule models that do not include intermolecular interactions do not account for several features.

Figure 12:
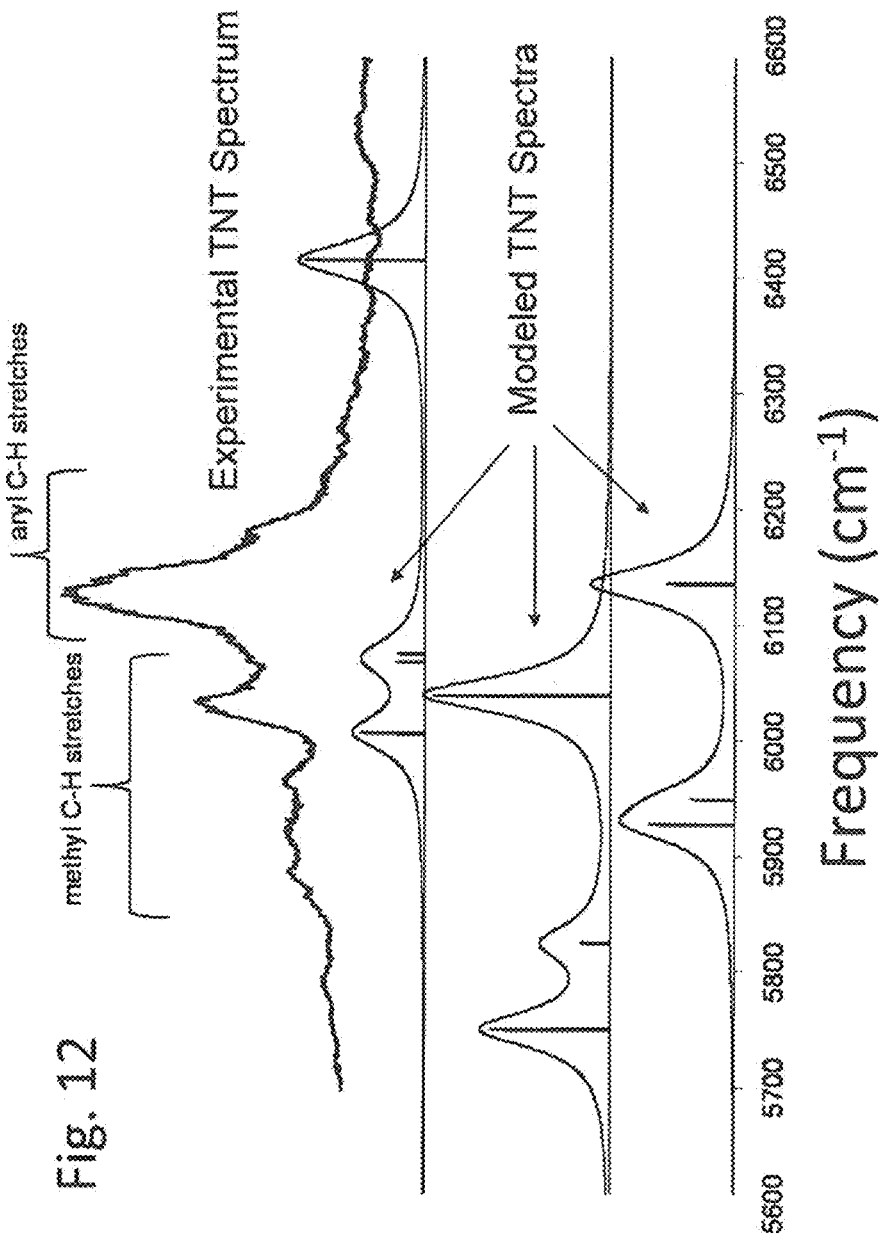
FIG. 12 is an illustration showing TNT overtone spectrum compared with predicted spectra from the local mode model for (1) HF/6-31+G(d,p), (2) DFT B3LYP/6-31+G(d.p). and (3) MP2/6-31+G(d,p). Harmonically Coupled Anharmonic Oscillators (HCAO) corrections to the predicted local mode frequencies are not shown in the predicted spectra.

When the spectra produced from single molecule models in FIG. 12 are compared with the TNT data in FIG. 11, it can be seen that the single molecule models for TNT do not account for the peak at 5956 cm$^{-1}$ or the shoulders around the main aryl C—H stretch peaks at 6104 or 6017 cm$^{-1}$. Although the spectra from the single molecule models have the same general shape as the laser photoacoustic overtone data and in some cases come within 20 cm$^{-1}$, of the measured aryl C—H stretches, there also is poor agreement for the methyl C—H stretching frequencies and intensities. The absence of several features in the predicted spectra shown in the predicted intensities of all three levels of theory in FIG. 12 can be explained by degeneracy in the highly symmetric single molecule models. Application of anharmonic corrections to the normal mode frequencies did not reproduce the additional features that appear in the experimental data. For a further investigation of this influence of the two-crystal polymorphs of TNT, see "Experimental and Theoretical Investigation of the First Overtone Spectrum of 1,3,5-Trinitrotoluene," by J. B. Cabalo and R. Sausa, The Journal of Physical Chemistry, Vol. 115, pages 9139-9150 (2011), hereby incorporated by reference.

Figure 13:
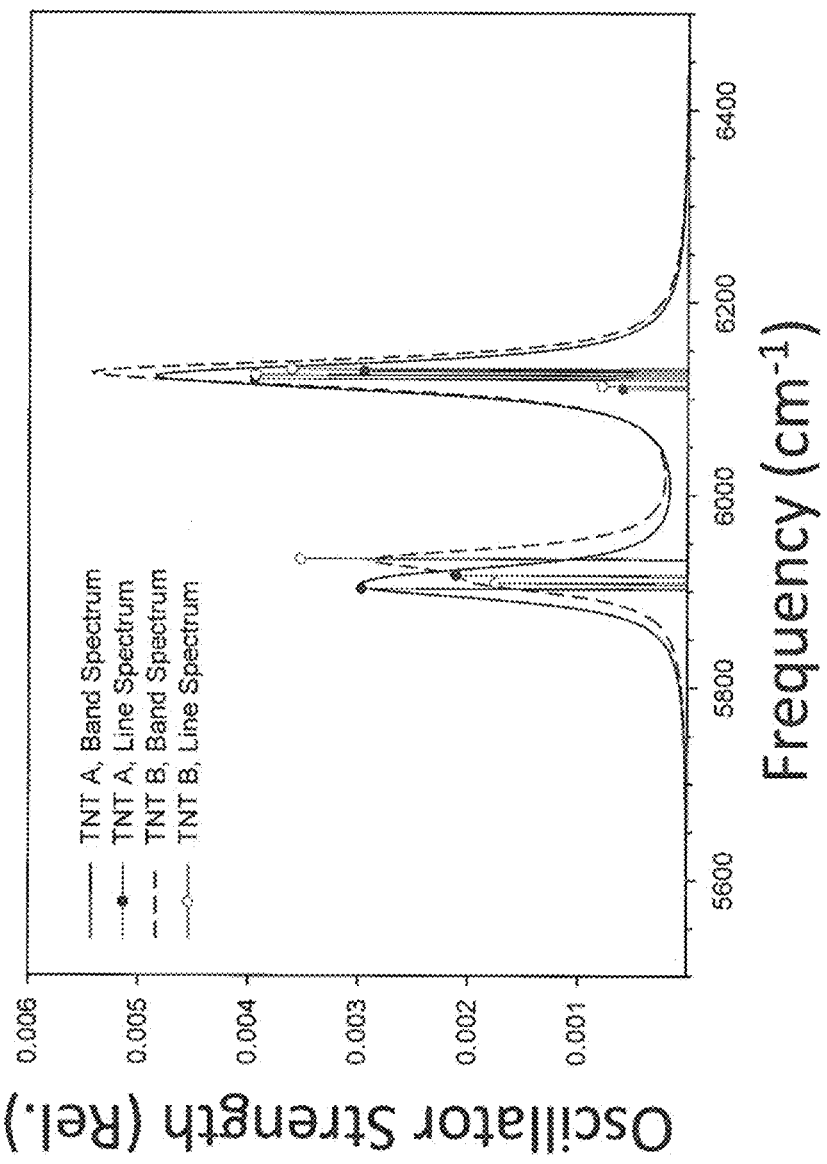
FIG. 13 is an illustration showing predicted spectra from single molecule models of A and B polymorphs reported from X-ray crystallography measurements.

To investigate the influence of the two crystal polymorphs of TNT as identified by X-ray crystallography, a single molecule model of each polymorph (denoted as "A" and "B") was optimized, and the HCAO analysis was applied. The nitro functional group dihedral angles of each respective model was set to match those measured with X-ray crystallography. The results are shown in FIG. 13, where the predicted overtone spectra are insensitive to the intramolecular geometry. The intramolecular O—H separations are comparable to the intermolecular O—H separations for both simulation and the X-ray measurements. The insensitivity to the positions of the intramolecular nitro functional groups makes sense because the electrostatic interactions were directed almost orthogonally to the axes of the C—H stretches, whereas the O—H intermolecular interactions were directed more closely along the C—H stretching axis, thus applying a greater perturbation. This result reinforces the fact that a multimolecular model was, indeed, necessary to interpret the experimental result.

Figure 14:
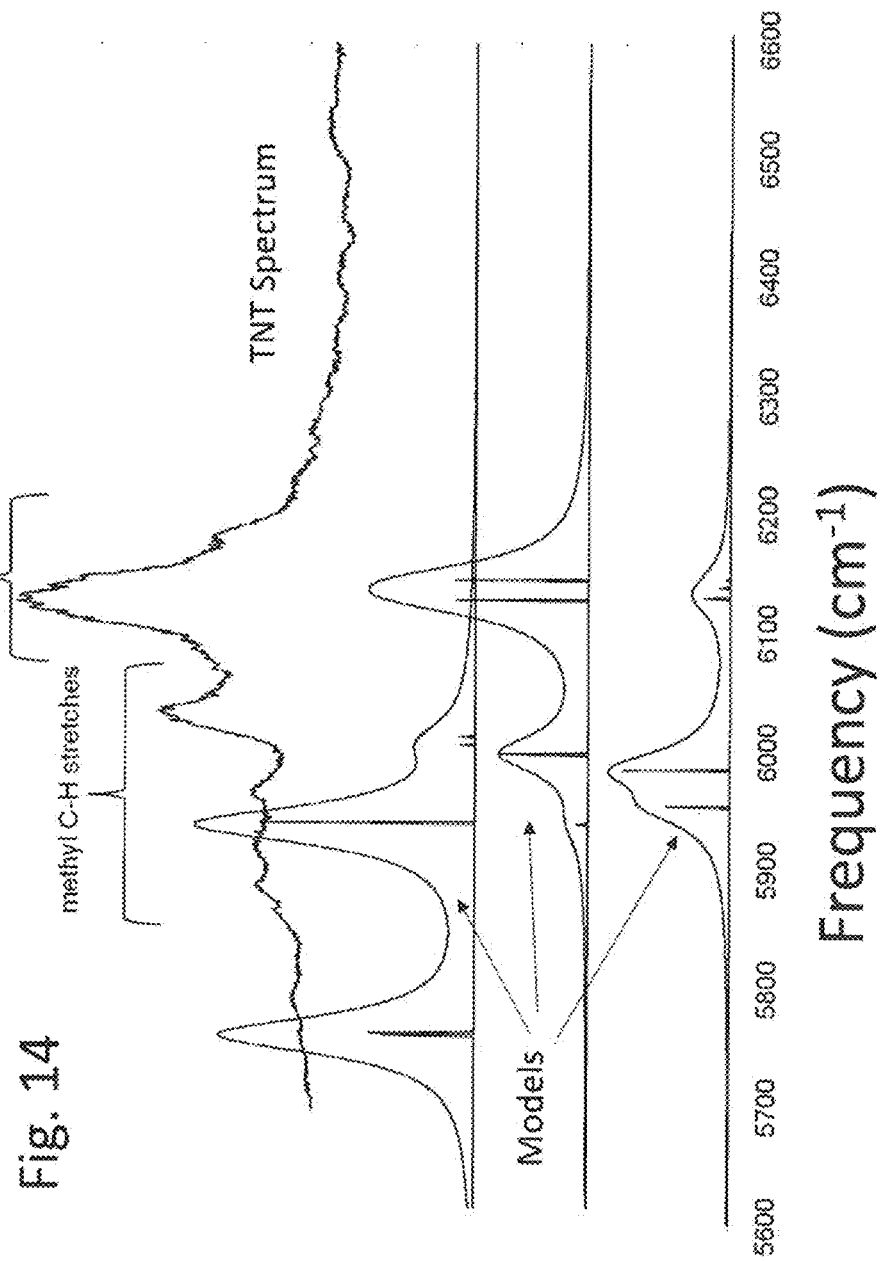
FIG. 14 is an illustration showing overtone spectra produced from eight member TNT molecule clusters.

The results of the predicted overtone spectra from the eight member cluster model are shown in FIG. 14. Although use of this simple cluster model eliminated the issue with degeneracy remaining differences between the predicted spectra and experiment show that the model inadequately captures the intermolecular interactions. The reason is that there was no position in the model that was completely caged by surrounding molecules, as occurs in the bulk crystal. It became clear that much improved results are obtained from the larger models that better simulate the TNT crystal. However, the eight molecule model yielded a key result. The results in FIG. 14 from the eight TNT molecule model show that the handling of electron correlation in the two-layer QM:MM models is critical. FIG. 14 is a comparison of predicted overtone spectra from the MP2/6-31+G(d,p) and B3LYP/6-31+G(d,p) levels of theory. When B3LYP/6-31+G(d,p) was used in the hybrid QM:MM eight molecule cluster model, it predicted a large drop in overtone intensity compared with the single molecule spectrum predicted in FIG. 12 such that the DFT predicted spectrum was attenuated by a factor of ~33. In contrast, the absorption intensities of the MP2/6-31+G(d,p)-predicted spectrum in FIG. 14 is in reasonable agreement with the predicted intensities of all three levels of theory in FIG. 12. The fact that the MP2-predicted spectra are not attenuated in the hybrid QM/MM models is quantitatively shown in Table 3 of the aforementioned J. B. Cabalo and R. Sausa article. The oscillator strengths predicted from the single unit cell model and the MP2 method agree with the single molecule oscillator strengths to within an order of magnitude. Comparison of the HCAO predicted Morse parameters is described in the J. B. Cabalo and R. Sausa article (see Table 2) provide additional insight into the reason the MP2 method gave better results.

FIG. 15 is an illustration of the laser photoacoustic overtone spectrum of TNT compared with predicted spectra from HCAO and the MP2/6-31+G(d,p) level of theory for charge assigned by the QEq/Mulliken, QEq/MSK, and HF/3-21+G* calculation/MSK. The model is optimized with the universal force field. A further description may be found in the J. B. Cabalo and R. Sausa article.

These aforementioned systems provide sensitive, accurate, and robust, detection of suspect materials substantially in "real-time" under ambient conditions. They may be invaluable for various applications, including detecting potential terrorist activity, demilitarization, and improvised explosive device (IEC) countermeasures, to name a few.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

While the foregoing is directed to embodiments of the present invention, other and further embodiments of the invention may be devised without departing from the basic scope thereof, and the scope thereof is determined by the claims that follow.

We claim:

1. A system for detecting materials comprising:
   (a) at least one laser configured to output light in the near infrared (IR) spectrum, the wavelength of the output laser light corresponding to a frequency associated with at least one vibrational overtone absorption transition, at least one combination band absorption transition, or a combination thereof, of a sample comprised of one or more materials so as to be absorbed and to excite the sample;
   (b) a detector configured to detect an excited physical phenomenon of the sample in response to absorption of the output laser light at the frequency associated with the at least one vibrational overtone absorption transition, the at least one combination band absorption transition, or the combination thereof; and
   (c) an analyzer configured to analyze the detected excited physical phenomenon and to identify the one or more materials based on comparison of the detected excited physical phenomenon with known signatures of the one or more materials.

2. The system of claim 1, wherein the at least one laser operates so as to output light having a wavelength between about 0.75 to 2.0 µm.

3. The system of claim 1, wherein said one or more materials are one or more of the following: explosives, propellants, chemical warfare agents, industrial pollutants or benign materials.

4. The system of claim 1, wherein said one or more materials are formulated with peroxides.

5. The system of claim 1, wherein said one or more materials are in a vapor phase.

6. The system of claim 1, wherein said one or more materials are in water.

7. The system of claim 1, wherein said one or more materials are residues on a surface.

8. The system of claim 1, wherein said one or more materials are in a liquid phase.

9. The system of claim 1, wherein the at least one laser is pulsed.

10. The system of claim 1, wherein the at least one laser is tunable.

11. The system of claim 1, wherein the at least one laser is continuous.

12. The system of claim 1, wherein the detector comprises a microphone.

13. The system of claim 12, further comprising an acoustic mirror to concentrate photoacoustic signals to the microphone.

14. The system of claim 1, wherein said detector is configured to measure or detect:
   (a) a change in pressure in the sample and/or its environment;
   (b) a change in temperature in the sample and/or its environment;
   (c) a change in the displacement of the sample and/or its environment;
   (d) a change in index of refraction in the sample and/or its environment;
   (e) a change in reflectivity in the sample and/or its environment; and/or
   (f) a change in light emission from the sample and/or environment.

15. The system of claim 1, wherein the at least one laser is configured to probe a change in the sample and/or its environment.

16. The system of claim 1, wherein said detector comprises a frequency filtering device, a signal digitizer, a signal analyzer, or any combination thereof.

17. A method for detecting and monitoring materials comprising:
   (a) exciting at least one vibrational overtone absorption transition, at least one combination band absorption transition, or a combination thereof, of a sample comprised of one or more materials using at least one laser which outputs light in the near infrared (IR) spectrum, the wavelength of the output laser light corresponding to a frequency associated with the at least one vibrational overtone absorption transition, at least one combination band absorption transition, or the combination thereof, of the sample;
   (b) detecting an excited physical phenomenon of the sample in response to absorption of the output laser light at the frequency associated with the at least one vibrational overtone absorption transition, the at least one combination band absorption transition, or the combination thereof; and
   (c) analyzing the detected excited physical phenomenon to identify the one or more materials based on comparison of the detected excited physical phenomenon with known signatures of the one or more materials.

18. The method of claim 17, wherein the at least one laser operates so as to output light having a wavelength between about 0.75 to 2.0 µm.

19. The method of claim 17, wherein said detecting comprises measuring or detecting:
   (a) a change in pressure in the sample and/or its environment;
   (b) a change in temperature in the sample and/or its environment;
   (c) a change in the displacement of the sample and/or its environment;
   (d) a change in index of refraction in the sample and/or its environment;
   (e) a change in reflectivity in the sample and/or its environment; and/or
   (f) a change in light emission from the sample and/or environment.

20. The method of claim 17, further comprising: operating the at least one laser to probe a change in the sample and/or its environment.

* * * * *